US007553638B2

(12) United States Patent
Nishiuchi et al.

(10) Patent No.: US 7,553,638 B2
(45) Date of Patent: *Jun. 30, 2009

(54) *CANDIDA UTILIS* CONTAINING γ-GLUTAMYLCYSTEINE

(75) Inventors: Hiroaki Nishiuchi, Kawasaki (JP); Yasushi Nishimura, Kawasaki (JP); Motonaka Kuroda, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 854 days.

This patent is subject to a terminal disclaimer.

(21) Appl. No.: 10/949,437

(22) Filed: Sep. 27, 2004

(65) Prior Publication Data

US 2005/0042328 A1 Feb. 24, 2005

Related U.S. Application Data

(63) Continuation of application No. PCT/JP03/03715, filed on Mar. 26, 2003.

(30) Foreign Application Priority Data

Mar. 26, 2002 (JP) ............................. 2002-085058

(51) Int. Cl.
*A23C 9/12* (2006.01)
(52) U.S. Cl. ........................................ 435/69.1; 426/42
(58) Field of Classification Search ........................ None
See application file for complete search history.

(56) References Cited

U.S. PATENT DOCUMENTS

| 2003/0124684 A1 | 7/2003 | Nishiuchi et al. |
| 2004/0214308 A1 | 10/2004 | Nishiuchi et al. |
| 2004/0247771 A1 | 12/2004 | Nishiuchi et al. |

FOREIGN PATENT DOCUMENTS

| JP | 61-31081 | 2/1986 |
| JP | 61-52299 | 3/1986 |
| JP | 4-91762 | 3/1992 |
| WO | WO 94/23015 | 10/1994 |
| WO | WO 94/24276 | 10/1994 |
| WO | WO 98/14600 | 4/1998 |
| WO | WO 01/90310 A1 | 11/2001 |

OTHER PUBLICATIONS

Rehm et al. II. Biomass from carbohydrates, Biotechnology vol. 3, pp. 29-30, 1983.*
Voet (D. Voet and J.G. Voet. Biochemistry, 2nd Edition.(1995), pp. 235-241.*
Database accession No. SCGSH11, "Saccharomyces Cerevisiae GSH1 Gene for Gamma-Glutamylcysteine Synthetase, Complete CDS.", Apr. 26, 1992, XP-002337689.
Database accession No. SCGSHGE, "Saccharomyces Cerevisiae GSH Gene Encoding Gamma-Glutamylcysteine Synthetase", Jun. 29, 1993, XP-002337690.
Database accession No. SPXXX002, "Schizosaccharomyces Pombe Gene for Gamma-Glutamyl-Cysteine Synthetase", Jun. 30, 1995, XP-002337691.
Database accession No. SPGCH1, "S. Pombe GCS1 Gene", Aug. 31, 1995, XP-002337692.
Database accession No. HSGCS, "Human Gamma-Glutamylcysteine Synthetase (GCS) MRNA, Complete CDS.", Apr. 4, 1992, XP-002337693.
European Office Action dated Jan. 12, 2009.
Database Emble [Online] Jan. 2, 2001, "Candida albicans gamma-glutamyl synthetase (GCS1) gene, complete" Retrieved from EMBL Accession No. AF176677 Database Accession No. AF176677.
Database Emble [Online] Jan. 12, 2001, "T7 end of clone of BD0AA010G07 of library DB0AA from strain CBS 94 of Candida tropicalis" Retrieved from EMBL Accession No. AL440211 Database Accession No. AL440211.
N. Mutoh, et al., "Molecular Cloning and Nucleotide Sequencing of the Gamma-Glutamylcysteine Synthetase Gene of the Fission Yeast Schizosaccharomyces Pombe", J. Biochem., vol. 117, No. 2, 1995, pp. 283-288.
A-L Wu, et al., "GSH1, Which Encodes Gamma-Glutamylcysteine Synthetase, Is A Target Gene for YAP-1 Transcriptional Regulation", Molecular and Cellular Biology, vol. 14, No. 9, Sep. 1994, pp. 5832-5839.
Y. Ohtake, et al., "Molecular Cloning of the Gamma-Glutamylcysteine Synthetase Gene of Saccharomyces Cerevisiae", Yeast, vol. 7, 1991, pp. 953-961.
R.J. Robins, et al., "The Role of Glutathione in Amino-Acid Absorption", Biochem. J., vol. 194, 1981, pp. 63-70.
U.S. Appl. No. 10/915,366, filed Aug. 11, 2004, Nishiuchi et al.
U.S. Appl. No. 10/949,437, filed Sep. 27, 2004, Nishiuchi et al.
U.S. Appl. No. 09/807,424, filed Oct. 15, 2001, Nishimura et al.
U.S. Appl. No. 10/307,431, filed Dec. 2, 2002, Kohmura et al.
U.S. Appl. No. 10/732,523, filed Dec. 11, 2003, Suehiro et al.
U.S. Appl. No. 10/853,183, filed May 26, 2004, Nishiuchi et al.
Yasuyuki Ohtake, et al., "Isolation and Characterization of Glutathione Biosynthesis-deficient Mutants in Saccharomyces Cerevisiae", Agric. Biol. Chem., vol. 54, No. 12, 1990, pp. 3145-3150.
Kenji Kondo, et al., "A Transformation System for the Yeast Candida utilis: Use of a Modified Endogenous Ribosomal Protein Gene a Drug-Resistant Marker and Ribosomal DNA as an Integration Target for Vector DNA", Journal of Bacteriology, vol. 177, No. 24, Dec. 1995, pp. 7171-7177.
Yasuyuki Otake, et al., "Glutathione Koseisan Kobo No Ikushu", Bioscience & Industry, vol. 50, No. 10, 1992, pp. 989-994 w/attached English Translation.

* cited by examiner

*Primary Examiner*—Jon P Weber
*Assistant Examiner*—Kagnew H Gebreyesus
(74) *Attorney, Agent, or Firm*—Oblon, Spivak, McClelland, Maier & Neustadt, P.C.

(57) ABSTRACT

Food containing γ-glutamylcysteine or cysteine is produced by culturing *Candida utilis* containing 1% by weight or more of γ-glutamylcysteine per dry cells in logarithmic growth phase when cultured in a minimal medium, for example, *Candida utilis* in which a gene encoding glutathione synthetase is modified so that intracellular glutathione synthetase activity is reduced, under a suitable condition and mixing the obtained culture or a fraction thereof or the culture or a fraction thereof subjected to heat treatment with a raw material of food or drink to process food or drink.

9 Claims, 5 Drawing Sheets

CANDIDA UTILIS CONTAINING γ-GLUTAMYLCYSTEINE

CROSS-REFERENCE TO A RELATED APPLICATION

The present application is a continuation application of PCT/JP03/03715, filed on Mar. 26, 2003, which claims priority to Japanese Patent Application No. JP 2002-85058. filed on Mar. 26, 2002.

TECHNICAL FIELD

The present invention relates to *Candida utilis* producing γ-glutamylcysteine and food utilizing the same. Gamma-glutamylcysteine and cysteine produced therefrom are useful in the food field.

BACKGROUND ART

Cysteine is used for the purpose of improving food flavor, taste etc. Among the known methods for producing cysteine, which are primarily used at present, are a proteolysis method and a semisynthesis method. In order to use cysteine for improvement of flavor and taste of food, it is required that a natural food material have a high content of cysteine. However, few natural food materials of such kind have been known heretofore. Meanwhile, it has been reported that a food material having a high content of cysteine can be obtained when yeast extract containing γ-glutamylcysteine is heated or treated with an enzyme (WO00/30474).

In *Saccharomyces cerevisiae*, γ-glutamylcysteine is synthesized by the action of γ-glutamylcysteine synthetase using cysteine and glutamic acid as substrates. Further, glutathione is synthesized by the action of glutathione synthetase using γ-glutamylcysteine and glycine as substrates. Yeasts having a high content of γ-glutamylcysteine have been reported in WO00/30474; Otake et al., Agri. Biol. Chem., 54 (12): 3145-3150 (1990); Chris et al., Molecular Biology of the Cell., 8, 1699-1707 (1997); Inoue et al., Biochimica et Biophysica Acta, 1395, 315-320 (1998) and so forth. However, all of these reports concern investigations using *Saccharomyces cerevisiae*, and there has been no report about investigations using *Candida utilis*.

*Candida utilis* has been previously classified in the genus *Pichia* or *Hansenula*, but is currently classified in the genus *Candida*. This genus *Candida* is one of 15 genera of imperfect yeasts, which do not carry out sexual reproduction or have not been found to carry out sexual reproduction, and is only a pickup genus in view of phylogenetic systematics ("Kobo Kenkyu Giho No Shintenkai", pp. 124-125 (ISBN: 4-7622-4670-0)). Yeasts of the genus *Candida* often have distinct characteristics in comparison with *Saccharomyces cerevisiae*. For example, *Candida utilis* has characteristics of obtaining most of its energy from the pentose phosphate cycle producing a pyridine base (Biotechnology, 3, 30 (1983) (ISBN: 3-527-25765-9)), weak catabolite repression (Biotechnology, 3, 30 (1983)) and so forth. Further, since *Saccharomyces cerevisiae* is usually used as a research yeast, there have been few findings about *Candida utilis*. Under such circumstances, there has been no report about how *Candida utilis* biosynthesizes glutathione, and there have been only reports that a specific *Candida utilis* obtained by utilizing zinc resistance or the like shows a temperature at which it produces a large amount of glutathione lower than the normally observed temperature by 5° C. or more (Japanese Patent Publication (Kokoku) No. 03-18872) etc.

Thus, the relationship between the glutathione synthetase activity and accumulation of γ-glutamylcysteine in *Candida utilis* remains unknown, and whether γ-glutamylcysteine can be accumulated by reducing the glutathione synthetase activity has been unclear.

DISCLOSURE OF THE INVENTION

It has been reported that the growth of *Candida utilis* per unit saccharide is better than that of *Saccharomyces cerevisiae* (Biotechnology, 3, 30 (1983)). Further, since it does not show ethanol byproduction under a strictly aerobic condition (Kondo et al. (J. Bacteriology, December, 1995, pp. 7171-7177)), there is less need of paying attention to the ethanol byproduction in its culture. Therefore, the inventors of the present invention considered that yeast extract produced by using *Candida utilis* having a high content of γ-glutamylcysteine would become less expensive than yeast extract produced by using *Saccharomyces cerevisiae* and hence desirable for industrial production.

The present invention was accomplished from the above viewpoint, and an object of the present invention is to provide *Candida utilis* having a high content of γ-glutamylcysteine, yeast extract produced by using the same, food containing γ-glutamylcysteine or cysteine produced by using them and a method for producing them.

The inventors of the present invention assiduously studied in order to achieve the above object. As a result, they successfully achieved γ-glutamylcysteine production in *Candida utilis* by obtaining a gene fragment that was expected to encode glutathione synthetase from *Candida utilis* based on homologies with those of other organisms and reducing a glutathione synthetase activity by utilizing this fragment. Further, they successfully obtained a gene fragment that was expected to encode γ-glutamylcysteine synthetase from *Candida utilis*, and thus accomplished the present invention.

The present invention essentially provides followings.

(1) *Candida utilis* which contains 1% by weight or more of γ-glutamylcysteine in dry cells in logarithmic growth phase when cultured in a minimal medium.

(2) The *Candida utilis* according to (1), wherein the minimal medium is SD medium.

(3) The *Candida utilis* according to (1) or (2), which shows glutathione synthetase activity of 0.005 μmol GSH/mg protein/hour or lower.

(4) The *Candida utilis* according to any one of (1) to (3), wherein a gene encoding glutathione synthetase is modified so that intracellular glutathione synthetase activity is reduced.

(5) The *Candida utilis* according to any one of (1) to (4), which is modified so that expression amount of a gene encoding γ-glutamylcysteine synthetase is increased.

(6) Food or drink comprising culture obtained by culturing the *Candida utilis* according to any one of (1) to (5) under a suitable condition, a fraction of the culture containing γ-glutamylcysteine, or the culture or the fraction in which cysteine is produced by heat treatment.

(7) The food or drink according to (6), which is a fermented food seasoning.

(8) Yeast extract produced by using culture obtained by culturing the *Candida utilis* according to any one of (1) to (5) under a suitable condition.

(9) A method for producing food containing γ-glutamylcysteine or cysteine, which comprises culturing the *Candida utilis* according to any one of (1) to (5) under a suitable condition and mixing the obtained culture or a fraction thereof or the culture or the fraction thereof subjected to a heat treatment with a raw material of food or drink to produce food or drink.

(10) A DNA which encodes a protein defined in the following (A) or (B):

(A) a protein which has the amino acid sequence of SEQ ID NO: 43;

(B) a protein which has the amino acid sequence of SEQ ID NO: 43 including substitution, deletion, insertion or addition of one or several amino acids, and has a γ-glutamylcysteine synthetase activity.

(11) The DNA according to (10), which is a DNA defined in the following (a) or (b):

(a) a DNA which comprises the nucleotide sequence of the nucleotide numbers 110 to 2101 of SEQ ID NO: 42;

(b) a DNA which is hybridizable with the nucleotide sequence comprising the sequence of the nucleotide numbers 110 to 2101 of SEQ ID NO: 42 or a probe that can be prepared from the nucleotide sequence under a stringent condition, and encodes a protein having a γ-glutamylcysteine synthetase activity.

BRIEF DESCRIPTION OF THE DRAWINGS

Brief Description of the Drawings

Figure 1:
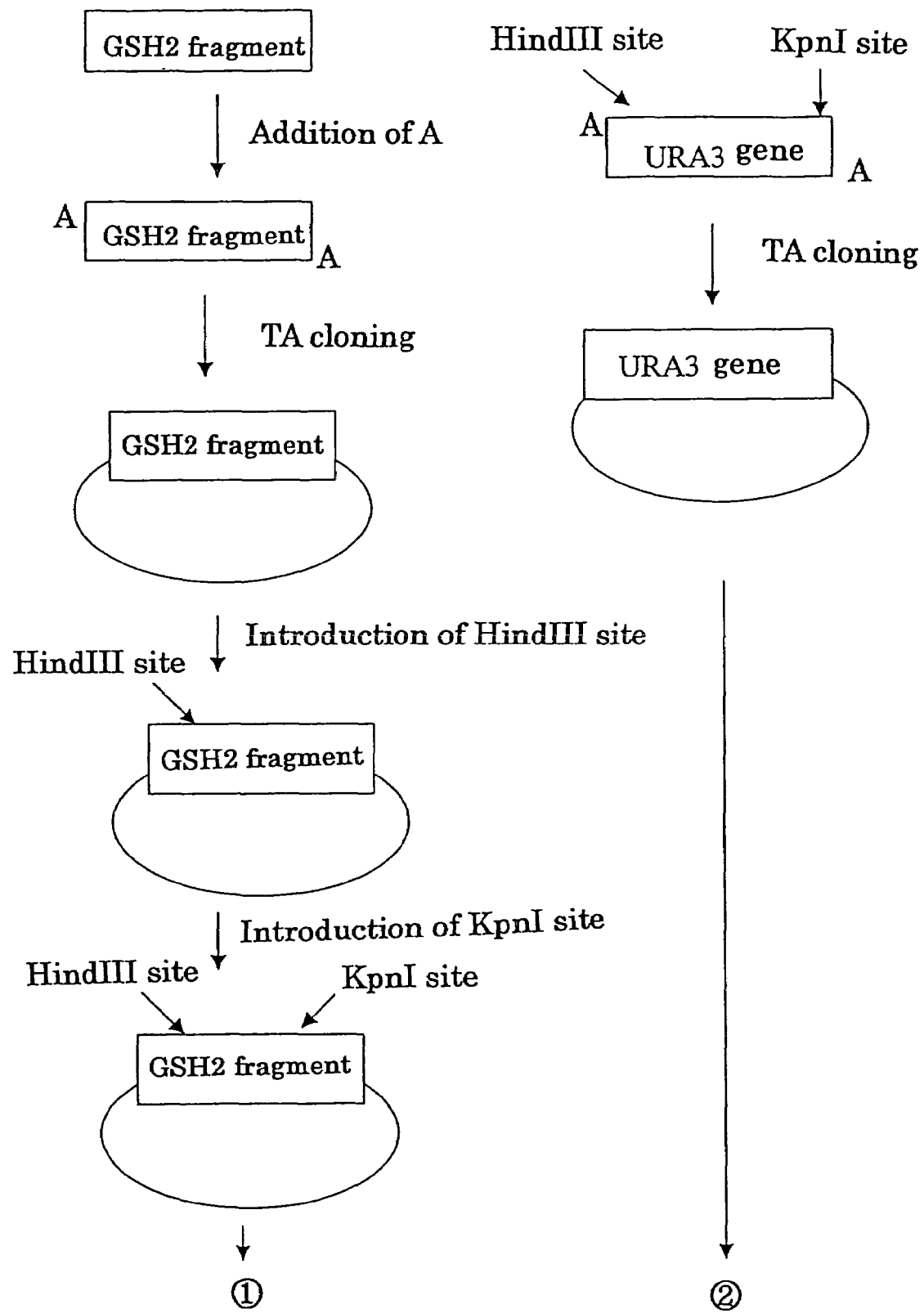

FIG. 1 shows construction (first half) of a glutathione synthetase gene disruption cassette for *Candida utilis*.

Figure 2:
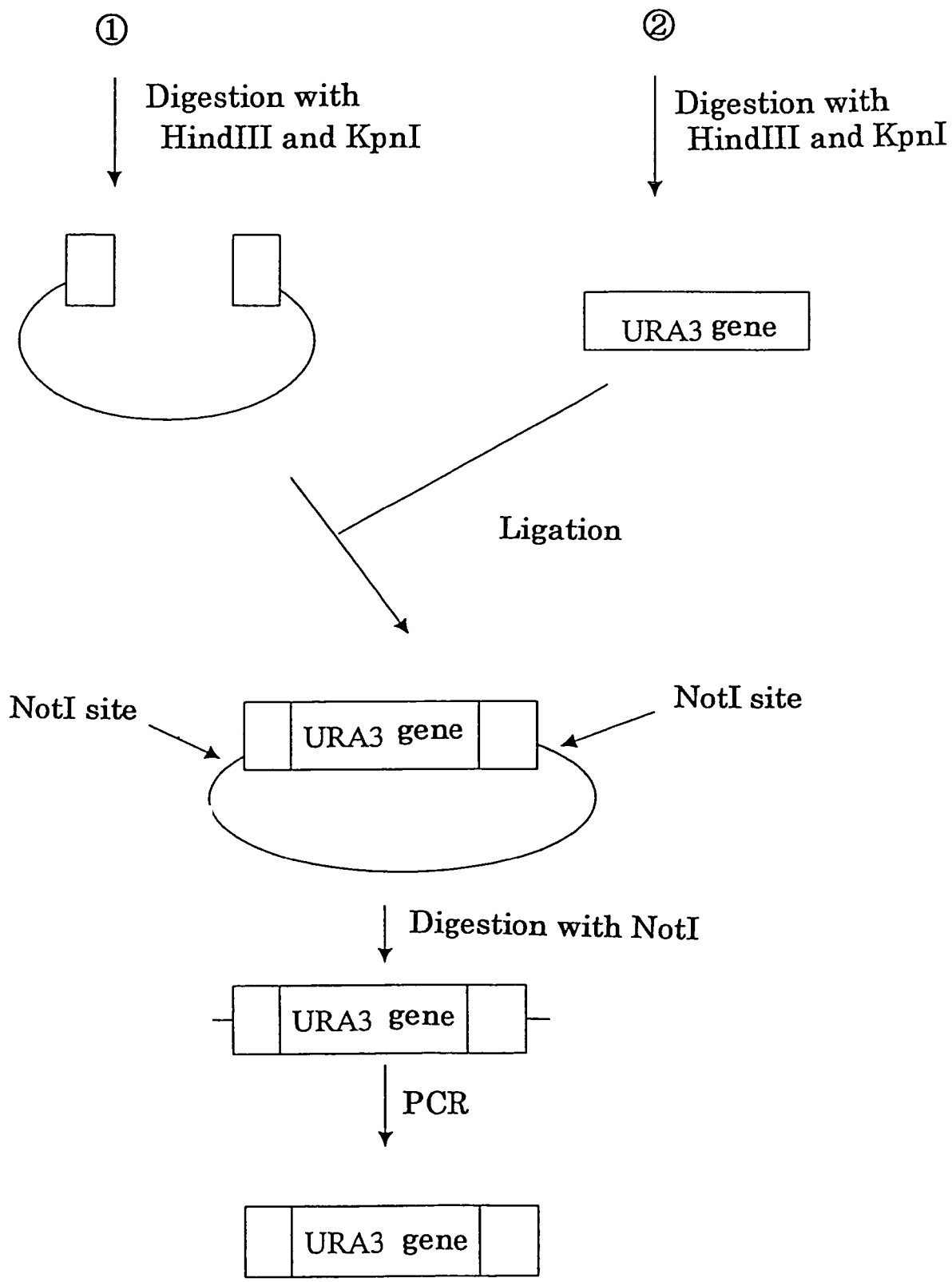

FIG. 2 shows construction (second half) of a glutathione synthetase gene disruption cassette for *Candida utilis*.

Figure 3:
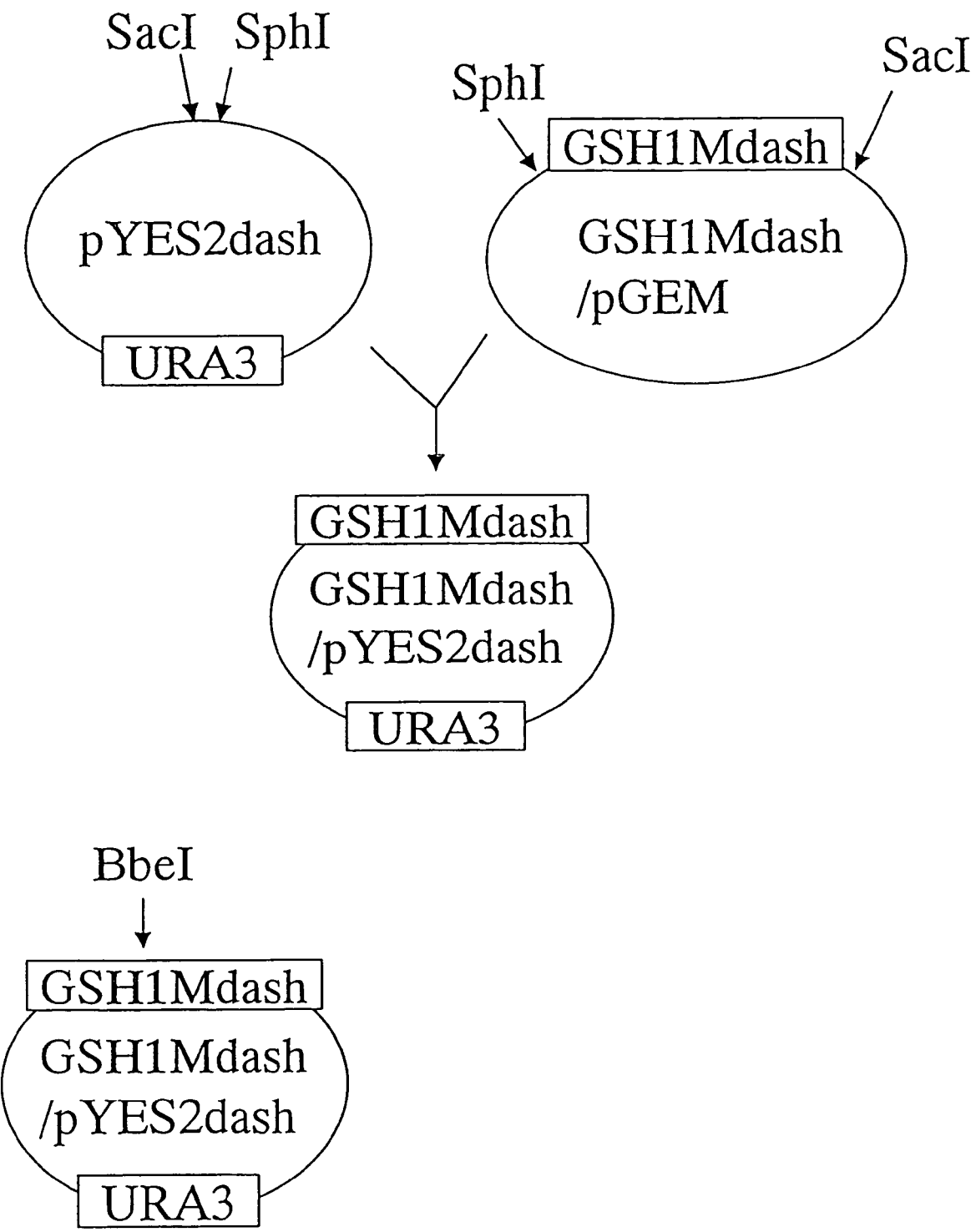

FIG. 3 shows construction of a γ-glutamylcysteine synthetase gene substitution cassette for *Candida utilis*.

Figure 4:
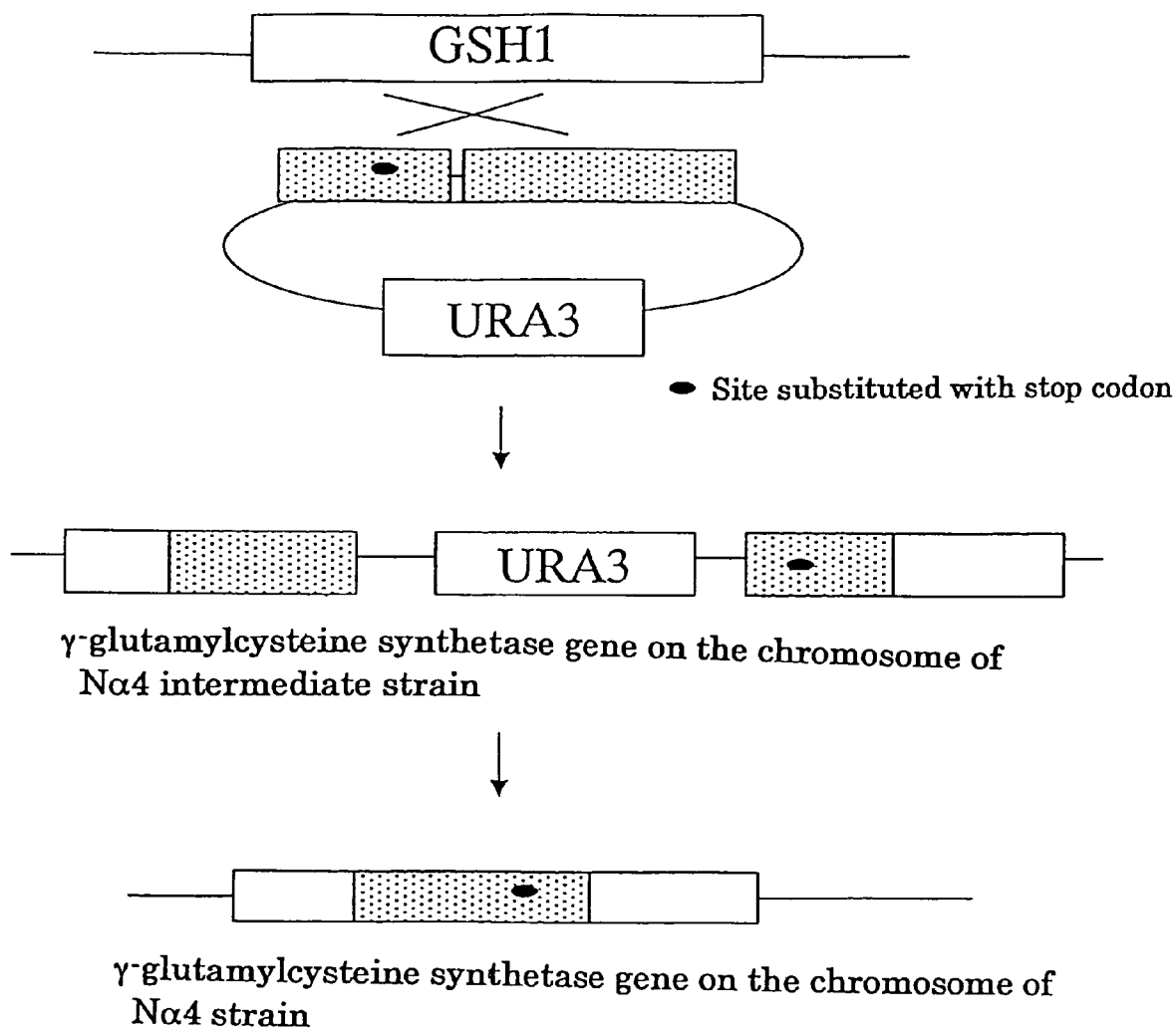

FIG. 4 shows construction of a γ-glutamylcysteine synthetase gene substituted strain of *Candida utilis*.

Figure 5:
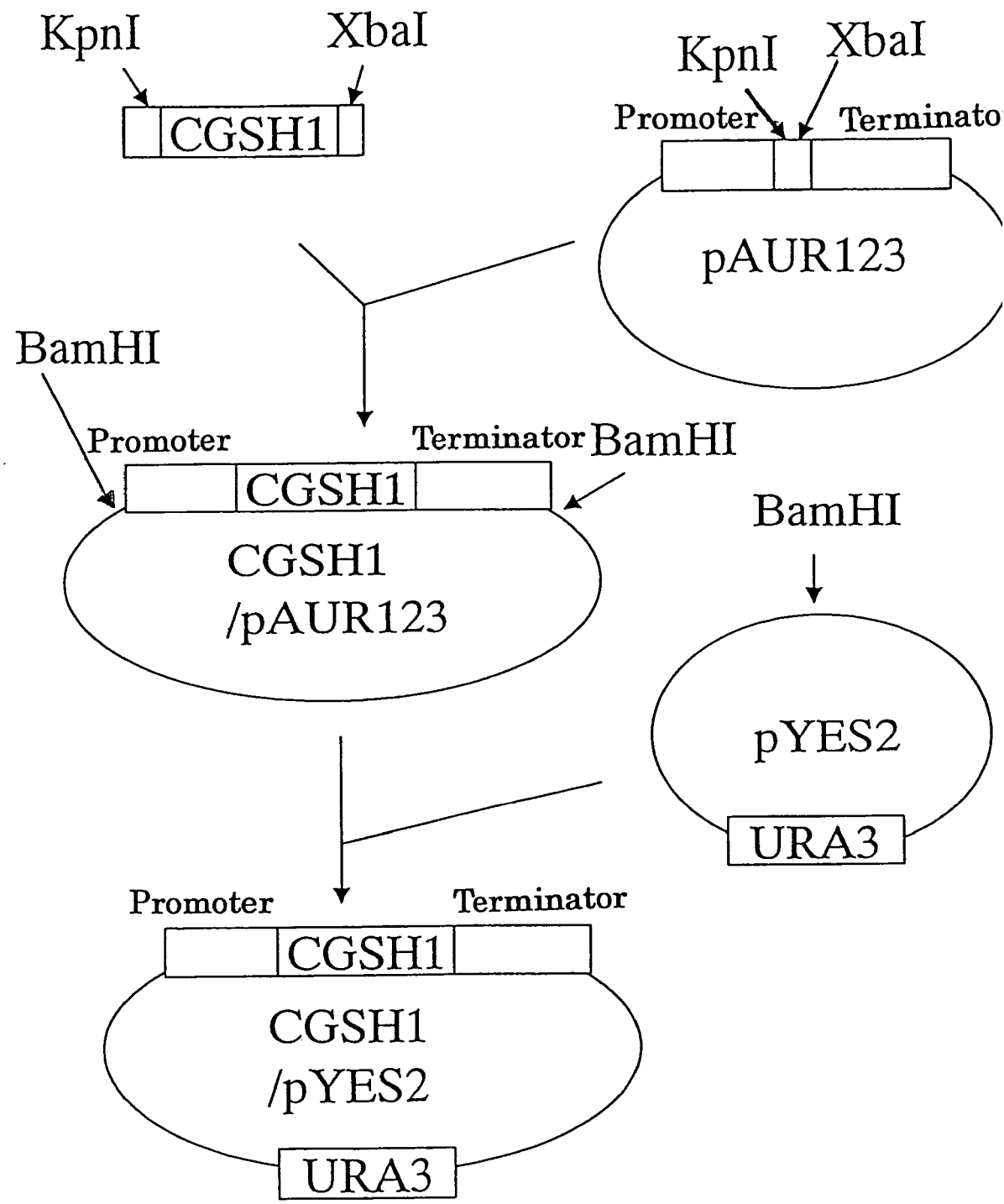

FIG. 5 shows construction of an expression vector of a γ-glutamylcysteine synthetase homologue derived from *Candida* utilis.

BEST MODE FOR CARRYING OUT THE INVENTION

Hereafter, the present invention will be explained in detail.

<1> *Candida utilis* of the Present Invention

*Candida utilis* of the present invention contains 1% by weight or more, preferably 1.5% by weight or more, more preferably 2.0% by weight or more, of γ-glutamylcysteine in dry yeast cells in the logarithmic growth phase when it is cultured in a minimal medium.

As the minimal medium, there can be mentioned SD medium having the following composition.

[Composition of SD Medium]
Glucose: 2%
Nitrogen Base: 1-fold concentration (Nitrogen Base having a 10-fold concentration is obtained by mixing 1.7 g of Bacto Yeast Nitrogen Base w/o Amino Acids and Ammonium Sulfate (Difco) and 5 g of ammonium sulfate, dissolving this mixture in 100 ml of sterilized water, adjusting the solution to about pH 5.2 and sterilizing the solution by filtration)

The term "logarithmic growth phase" refers to a period in which the number of cells in the culture logarithmically increases relative to the culture time. Although the culture may be shaking culture or stationary culture, shaking culture is preferred.

The content of γ-glutamylcysteine is the content (%) of γ-glutamylcysteine based on the weight of dry yeast cells, that is, solid components of cells, for example, cells after heating at 105° C. for 4 hours.

The aforementioned γ-glutamylcysteine content does not need to be maintained over the entire logarithmic growth phase, and it is sufficient that the above value is shown at least at any point of the logarithmic growth phase, preferably in the logarithmic growth phase showing the following state. That is, the aforementioned state is a logarithmic growth phase in which the culture broth shows an absorbance higher than a half of the absorbance of the culture broth in the stationary phase just after the logarithmic growth phase.

The *Candida utilis* of the present invention preferably shows a glutathione synthetase activity of 0.005 μmol GSH/mg protein/hour or lower, more preferably 0.001 μmol GSH/mg protein/hour or lower ("GSH" represents glutathione). It is further preferred that the glutathione synthetase activity should be below the detection limit. The glutathione synthetase activity can be measured by the method of Gushima et al. (T. Gushima et al., J. Appl. Biochem., 5, 210 (1983)).

The *Candida utilis* of the present invention can be obtained by modifying an appropriate strain, for example, a wild type strain, of *Candida utilis*, by mutagenesis treatment or a gene recombination technique (for example, the techniques disclosed in the following publications can be utilized: FEMS Microbiology Letters, 165, 335-340 (1998); J. Bacteriology, December 1995, pp. 7171-7177; Curr. Genet. 10 (8): 573-578 (1986); WO98/14600) so that the intracellular glutathione synthetase activity should be reduced. The reduction of the glutathione synthetase activity includes elimination of the glutathione synthetase activity. Further, *Candida utilis* containing γ-glutamylcysteine can also be bred by modifying a strain so that the intracellular γ-glutamylcysteine synthetase activity should be increased. The γ-glutamylcysteine synthetase activity can be measured by the method of Jackson (R. C. Jackson, Biochem. J., 111, 309 (1969)).

As the mutagenesis treatment, there can be mentioned a treatment by ultraviolet ray irradiation, or a treatment using a mutagenesis agent used for usual mutagenesis treatment such as MNNG, ethylmethanesulfonate (EMS) or methylmethanesulfonate (MMS).

Further, as a method for reducing the glutathione synthetase activity by utilizing a gene recombination technique, a method of modifying a gene encoding glutathione synthetase so that the glutathione synthetase activity should be reduced may be used. A nucleotide sequence of a part of the gene encoding glutathione synthetase of the *Candida utilis* ATCC15239 strain is shown as SEQ ID NO: 17.

Notably, the glutathione synthetase gene from yeast of the genus *Candida* was not previously known. The inventors of the present invention searched amino acid sequences of glutathione synthetase of various organisms for a highly conserved region and found the regions of SEQ ID NOS: 1 to 8. Then, they successfully amplified a gene fragment that was expected to encode glutathione synthetase from chromosomal DNA of *Candida utilis* by performing PCR using primers corresponding to the amino acid sequences of SEQ ID NOS: 6 to 8 among the aforementioned regions. The primers of SEQ ID NOS: 15 and 16 can Further, the *Candida utilis* strain is not particularly limited, but the ATCC 15239 strain of *Candida utilis* can be mentioned as an exemplary strain. This strain can be obtained from American Type Culture Collection (Address: 10801 University Boulevard, Manassas, VA 20110-2209, United States of America). A method of modifying an expression regulatory sequence of the gene encoding glutathione synthetase so that the expression of glutathione synthetase should be reduced, or modifying the coding region so that glutathione synthetase having an activity should not be expressed are two examples of the method for reducing the glutathione synthetase activity by modifying a gene encoding glutathione synthetase in the present invention. Specifically, for example, the gene on the chromosome can be disrupted by transforming *Candida utilis* with recombinant DNA including a mutant glutathione synthetase gene of which 5' and 3' ends are deleted and inducing recombination between the mutant gene and the wild-type gene on the chromosome. In this method, operations become easier if a marker gene is included in the recombinant DNA according to a characteristic of a host such as auxotrophy. Further, if the recombinant DNA is linearized beforehand by digestion with a restriction enzyme or the like, a strain in which the recombinant DNA is incorporated into the chromosome can be efficiently obtained.

Further, the gene on the chromosome can also be disrupted by introducing recombinant DNA including a mutant gene modified so as not to produce normally functioning glutathione synthetase by deleting a internal region in the glutathione synthetase gene into *Candida utilis* and inducing recombination between the mutant gene and the normal gene on the chromosome.

In the strain in which the recombinant DNA is incorporated into the chromosome as described above, recombination is caused with a glutathione synthetase gene sequence that originally exists on the chromosome, and thereby two of fusion genes of the wild-type glutathione synthetase gene and the mutant glutathione synthetase gene are inserted into the chromosome so as to sandwich the other portions of the recombinant DNA (vector portion and marker gene). Therefore, the wild-type glutathione synthetase gene functions in this state.

Subsequently, in order to leave only the mutant glutathione synthetase gene on the chromosomal DNA, one copy of the glutathione synthetase gene is eliminated from the chromosomal DNA together with the vector portion (including the marker gene) by recombination of two of the glutathione synthetase genes. After this step, the wild-type glutathione synthetase gene is left on the chromosomal DNA, and the mutant glutathione synthetase gene is excised, or conversely, the mutant glutathione synthetase gene is left on the chromosomal DNA, and the wild-type glutathione synthetase gene is excised. Since the marker gene is eliminated in either case, occurrence of the second recombination can be confirmed based on a phenotype corresponding to the marker gene. Further, a target gene-substituted strain can be selected by amplifying the glutathione synthetase gene by PCR and examining its structure.

As the glutathione synthetase gene or a fragment thereof used for the gene disruption, in addition to DNA having the nucleotide sequence of SEQ ID NO: 17, there can be mentioned DNA hybridizable with this nucleotide sequence under a stringent condition and DNA having homology of 90% or more, preferably 95% or more, more preferably 99% or more, with the nucleotide sequence of SEQ ID NO: 17. The stringent condition is exemplified by a condition under which DNAs are hybridized with each other at a salt concentration corresponding to an ordinary condition of washing in Southern hybridization, i.e., 1×SSC, 0.1% SDS, preferably 0.1× SSC, 0.1% SDS, at 60° C.

The disruption of the glutathione synthetase gene of *Saccharomyces cerevisiae* is disclosed in WO00/30474.

Examples of the method for introducing the recombinant DNA into *Candida utilis* include the electroporation method (Luis et al., FEMS Microbiology Letters, 165, 335-340 (1998)).

The strain in which glutathione synthase activity is reduced can be selected by using susceptibility to methylglyoxal as index (Y. Ohtake et al., Agri. Biol. Chem., 54 (12): 3145-3150 (1990)). A strain that can biosynthesize a certain amount of glutathione (a strain having the glutathione synthetase activity and γ-GC synthetase activity) exhibits resistance to methylglyoxal. Further, the reduction of the glutathione synthetase activity can also be confirmed by examining the growth in a medium not containing glutathione. Further, a strain having a reduced glutathione synthetase activity can be efficiently obtained by utilizing an MNNG (N-methyl-N'-nitro-N-nitrosoguanidine) concentration gradient plate.

Reduction of glutathione synthetase activity can be confirmed by the following exemplary method. A filter was placed at the center of a YPD agar plate, and the whole amount of a solution of 1 mg MNNG dissolved in 30 μl of DMSO was infiltrated into the filter to prepare an MNNG concentration gradient agar medium, in which the MNNG concentration becomes lower at a position further from the center point. A haploid Nα1 strain and Nα3 strain of *Saccharomyces cerevisiae* cultured in the YPD medium were spread on the above agar medium. After the culture at 30° C. for 70 hours, the distances from the center of the agar medium to a position at which the yeasts formed a colony were measured. As a result, the distance for the Nα1 strain was 2.3 cm, and that for the Nα3 strain was 1.8 cm. The Nα3 strain is a strain obtained by modifying the Nα1 strain as a parent strain so that the sequence from and after the 370 th arginine residue of glutathione synthetase should be deleted. Therefore, the Nα3 strain is characterized by having attenuated glutathione synthetase and containing only a trace amount of glutathione.

The *Candida utilis* of the present invention may have an enhanced γ-glutamylcysteine synthetase activity in addition to the reduced glutathione synthetase activity. The γ-glutamylcysteine synthetase activity can be enhanced by introducing the γ-glutamylcysteine synthetase gene into *Candida utilis* in a form that can be expressed. Examples of the γ-glutamylcysteine synthetase gene include, for example, the gene derived from *Saccharomyces cerevisiae* and the gene derived from *Candida utilis*, which will be described later.

Examples of the method for introducing the γ-glutamylcysteine synthetase gene into *Candida utilis* include, for example, a method of transforming *Candida utilis* with recombinant DNA including this gene and a DNA sequence existing on the *Candida utilis* chromosome to incorporate the recombinant DNA into the chromosome (K. Kondo et al., J. Bacteriol., 177, 7171-7177 (1995)). Specifically, the introduction can be performed in the same manner as the aforementioned gene substitution.

Further, a target gene-can also be introduced into *Candida utilis* by using a plasmid including an autonomously replicable sequence (ARS) existing in the chromosomal DNA. The ARS of *Candida utilis* and the transformation using the same are described in International Patent Publication WO95/32289.

As the method for transformation of *Candida utilis*, usual methods employed for transformation of yeast such as the protoplast method, KU method (H. Ito et al., J. Bateriol., 153-163 (1983)), KUR method (Hakko to Kogyo (Fermentation and Industry), 43, 630-637 (1985)) and electroporation method can be employed. Further, operations of sporulation of yeast, isolation of haploid yeast etc. are described in "Chemistry and Biology, Experiment Line, vol. 31, Experimental Techniques for Yeast", First Edition, Hirokawa Shoten, "Biomanual Series 10, Genetic Experiment Using Yeast", First Edition, Yodosha and so forth.

Further, examples of the method for enhancing the γ-glutamylcysteine synthetase activity in a *Candida utilis* cell include a method of replacing a promoter of the γ-glutamylcysteine synthetase gene on the chromosome with a strong transcription promoter (Y. Ohtake et al., Bioscience and Industry, 50 (10) 989-994 (1992)) can be mentioned.

<2> Gamma-glutamylcysteine Synthetase Gene of *Candida utilis*

The DNA of the present invention is a DNA which encodes a protein defined in the following (A) or (B):
(A) a protein which has the amino acid sequence of SEQ ID NO: 43;
(B) a protein which has an amino acid sequence of SEQ ID NO: 43 including substitution, deletion, insertion or addition of one or several amino acids, and has a γ-glutamylcysteine synthetase activity.

The term "γ-glutamylcysteine synthetase activity" refers to an activity of catalyzing a reaction for producing γ-glutamylcysteine from cysteine and glutamic acid.

The γ-glutamylcysteine synthetase encoded by the DNA of the present invention may include substitution, deletion, insertion, addition or inversion of one or several amino acids at one or more sites in the amino acid sequence of SEQ ID NO: 43 so long as the aforementioned enzymatic activity thereof is not degraded. Although the number of "several" amino acids referred to herein differs depending on position or type of amino acid residues in a three-dimensional structure of the protein, it may be specifically 2 to 15, preferably 2 to 8, more preferably 2 to 5.

A DNA encoding a protein substantially identical to the aforementioned γ-glutamylcysteine synthetase can be obtained by modifying the nucleotide sequence by, for example, site-directed mutagenesis so that amino acid residues at a specific site should include substitution, deletion, insertion, addition or inversion. Further, such a DNA modified as described above can also be obtained by a known mutagenesis treatment. Examples of the mutagenesis treatment include a method of treating a DNA encoding γ-glutamylcysteine synthetase in vitro with hydroxylamine or the like and a method of treating a microorganism containing a DNA encoding γ-glutamylcysteine synthetase, for example, a bacterium of the genus *Escherichia*, with ultraviolet ray irradiation or a mutagenesis agent used in usual mutagenesis such as N-methyl-N'-nitro-N-nitrosoguanidine (NG) or EMS.

Further, the aforementioned substitution, deletion, insertion, addition, inversion or the like of amino acid residues includes a mutation (mutation or variation) that naturally occurs, for example, a mutation attributable to a difference in *Candida utilis* strains containing γ-glutamylcysteine synthetase.

The DNA encoding a protein substantially identical to γ-glutamylcysteine synthetase can be obtained by expressing a DNA having such a mutation as described above in a suitable cell of Saccharomyces cerevisiae or the like and examining the γ-glutamylcysteine synthetase activity in the cell. Further, the DNA encoding a protein substantially identical to γ-glutamylcysteine synthetase can also be obtained by, for example, isolating a DNA which is hybridizable with a probe having the nucleotide sequence of SEQ ID NO: 42 or a part thereof under a stringent condition and encoding a protein having a γ-glutamylcysteine synthetase activity from a DNA encoding γ-glutamylcysteine synthetase having a mutation or a cell containing the same. The "stringent condition" referred to herein is a condition under which a so-called specific hybrid is formed, and a non-specific hybrid is not formed. It is difficult to clearly express this condition by using any numerical value. However, for example, the stringent condition includes a condition under which DNAs having high homology, for example, DNAs having homology of 75% or more, preferably 85% or more, more preferably 95% or more, are hybridized with each other, but DNAs having homology lower than the above are not hybridized with each other. More specifically, the stringent condition is exemplified by a condition under which DNAs are hybridized with each other at a salt concentration corresponding to an ordinary condition of washing in Southern hybridization, i.e., 1×SSC, 0.1% SDS, preferably 0.1×SSC, 0.1% SDS, at 60° C.

As the probe, a part of the nucleotide sequence of SEQ ID NO: 42 can also be used. Such a probe can be prepared by PCR using oligonucleotides prepared based on the nucleotide sequence of SEQ ID NO: 42 as primers and a DNA fragment including the nucleotide sequence of SEQ ID NO: 42 as a template. When a DNA fragment having a length of about 300 bp is used as the probe, a condition of washing in hybridization may be consist of, for example, 2×SSC, 0.1% SDS, at 50° C.

The genes hybridized under the aforementioned condition include those in which a stop codon is generated or those deficient in the activity due to the mutation. However, these can be selected by examining the enzymatic activity of the expression product.

The DNA having the nucleotide sequence of SEQ ID NO: 42 was confirmed to encode γ-glutamylcysteine synthetase, since glutathione synthesis was accelerated by its introduction into *Saccharomyces cerevisiae* having attenuated γ-glutamylcysteine synthetase as shown in the examples described later.

As a result of homology search of the amino acid sequence of SEQ ID NO: 42 in a database, it showed homologies of 50.93% and 42.88% with the amino acid sequences of γ-glutamylcysteine synthetases of *Saccharomyces cerevisiae* and *Schizosaccharomyces pombe*, respectively.

<3> Yeast Extract and Food or Drink of the Present Invention and Method for Producing the Same The culture obtained by culturing the yeast producing γ-glutamylcysteine obtained as described above under a suitable condition or a fraction thereof contains γ-glutamylcysteine. The culture may be a culture broth containing yeast cells, or yeast cells, disrupted cells or cell extract (yeast extract) obtained from the culture. Alternatively, a fraction containing γ-glutamylcysteine may be obtained from disrupted cells or yeast extract.

Since γ-glutamylcysteine is decomposed into cysteine and pyrrolidonecarboxylic acid when the aforementioned culture containing γ-glutamylcysteine or a fraction thereof is heated, cysteine can be released. Specifically, cysteine can be produced by maintaining the culture or a fraction thereof in the presence of water in an acidic to neutral condition, specifically at pH 1 to 7 at 50 to 120° C. for 3 to 300 hours.

Further, cysteine can also be produced by adjusting the culture containing γ-glutamylcysteine or a fraction thereof to pH 3 to 9, adding a γ-glutamyl peptide decomposing enzyme (γ-glutamyltransferase, γ-glutamylcyclotransferase, glutaminase etc.) and allowing it to act on the γ-glutamylcysteine at 15 to 70° C. for 1 to 300 minutes.

The medium used for the culture is not particularly limited so long as the yeast of the present invention favorably grows and γ-glutamylcysteine is efficiently produced. If required, necessary nutrients are added to the medium depending on the characteristics of the yeast.

The culture conditions, the preparation of the yeast extract and the like can be performed in the same manner as those in usual culture of yeast or usual preparation of yeast extract. The yeast extract may be extracted from yeast cells with hot water or obtained by digesting yeast cells. Further, the yeast extract of the present invention may be used after heat treatment or enzymatic treatment, or may be subjected to heat treatment when or after it is processed into food or drink with other raw materials of the food or drink.

Specifically, the heat treatment of the yeast extract can be performed as follows. Water is added to yeast extract powder, and the mixture is adjusted to pH 5 with hydrochloric acid to prepare an aqueous solution at a concentration of 2%. Then, this solution is heated at 98° C. for 180 minutes.

The culture containing γ-glutamylcysteine or cysteine or a fraction thereof can be used for production of food or drink. Examples of the food or drink include alcohol drink, breads, and fermented food seasonings can be mentioned. Production of cysteine from γ-glutamylcysteine by a heat treatment may be performed during or after the production of the food or drink. Further, prior to the production of the food or drink, the yeast culture or a fraction thereof may be subjected to a heat treatment.

The aforementioned food or drink is produced by mixing a culture containing γ-glutamylcysteine or cysteine or a fraction thereof with raw materials of the food or drink and processing the mixture into the food or drink. The food or drink of the present invention can be produced by using the same raw materials as those of usual food or drink by a similar method except for using the aforementioned culture or the fraction. Examples of such raw materials include rice, barley, corn starch and so forth for alcohol drinks, wheat flower, sugar, salt, butter, yeast for fermentation and so forth for breads, and soybean, wheat and so forth for fermented food seasonings. Further, yeast extract or its concentrate, or dried products of these can be used as they are as a fermented food seasoning.

EXAMPLES

The present invention will be explained more specifically with reference to the following examples.

EXAMPLE 1

Construction of *Candida utilis* Producing γ-glutamylcysteine

<1> Acquisition of Gene Fragment Expected to Code for Glutathione Synthetase of *Candida utilis*

The *Candida utilis* ATCC15239 strain was cultured at 30° C. with shaking in a YPD test tube medium, and chromosome was recovered from the cells by using Dr. GenTLE for Yeast (Takara Shuzo, Code 9084).

[Composition of YPD medium]

| | |
|---|---|
| Glucose | 2% |
| Peptone | 2% |
| Yeast extract | 1% |
| (pH 5.0) | |

The following sequences showing high homology were selected from amino acid sequences of glutathione synthetases of *Saccharomyces cerevisiae, Schizosaccharomyces pombe* and rat (for these, Chris et al., Molecular Biology of the Cell., 8, 1699-1707 (1997)).

| (i) | QEVAVVYYR | (SEQ ID NO: 1) |
| (ii) | GSKKIQQ | (SEQ ID NO: 2) |
| (iii) | VLKPQREGGGNN | (SEQ ID NO: 3) |
| (iv) | ISELGIYG | (SEQ ID NO: 4) |
| (v) | GGVAAGF | (SEQ ID NO: 5) |

Degenerated primers were designed based on these amino acid sequences, and degenerated PCR was performed by using degenerated primers corresponding to each pair of (i) and (ii), (i) and (iii), (i) and (iv), (i) and (v), (ii) and (iii), (ii) and (iv), (ii) and (v), (iii) and (iv), (iii) and (v), and (iv) and (v). Each PCR product was subjected to agarose gel electrophoresis, and a region for the expected size was excised to recover DNA. Further, although nested PCR was performed by using this recovered DNA as a template, a target fragment could not be obtained.

Subsequently, primers corresponding to the following amino acid sequences were designed with reference to the frequency of codons used in *Candida utilis*.

| (vi) | GSKKIQQ | (SEQ ID NO: 6) |
| (vii) | EGGGNN | (SEQ ID NO: 7) |
| (viii) | PQREGGG | (SEQ ID NO: 8) |

PCR was performed by using a primer corresponding to the amino acid sequence of the above (vi) (GGT TCY AAG AAG ATY CAR CA, SEQ ID NO: 9) and a primer corresponding to the amino acid sequence of the above (vii) (CCA CCA CCY TCT CTY TGT GG, SEQ ID NO: 10). PCR was performed by using KOD Dash (TOYOBO, Code LDP-101) according to the manufacturer's instruction with the conditions of a reaction at 94° C. for 2 minutes, followed by reactions at 94° C. for 1 minute, 55° C. (lowering temperature by 0.5° C. at each cycle) for 1 minute and 74° C. for 40 seconds repeated for 22 cycles and reactions at 94° C. for 1 minute, 50° C. for 1 minute and 74° C. for 40 seconds repeated for 15 cycles.

The PCR product was subjected to agarose gel electrophoresis (Nusieve 3:1 agarose 3%, 1×TAE solution (Takara Shuzo, Code F5180A)). The gel was stained by using an ethidium bromide solution, then a region corresponding to 100 to 300 bp was excised, and DNA was recovered from the gel by using MagExtractor (TOYOBO, Code NPK-601).

When nested PCR was performed by using this DNA as a template, a primer corresponding to the region of (vi) (SEQ ID NO: 9) and a primer designed so as to correspond to the region of (viii) (GTT GTT ACC ACC ACC YTC, SEQ ID NO: 11), three bands were detected in the region corresponding to 100 to 300 bp. PCR was performed under the same condition as described above. These three bands were each excised, and DNA was recovered from the gel. DNA of each band was ligated to a pGEM-T Easy vector (Promega) by using DNA Ligation Kit Ver. 2 (Takara Shuzo) and used to transform *Escherichia coli* JM109 competent cells (Takara Shuzo, Code 9052). Among the obtained transformants, one of transformant was obtained as a transformant expected to contain a gene fragment expected to encode glutathione synthetase of Candida utilis. The nucleotide sequence of the insert included in the transformant was determined in a conventional manner.

3' Rapid amplification of cDNA ends (RACE) was performed based on the nucleotide sequence determined as described above by using 3'-RACE System for Rapid Amplification of cDNA Ends (Gibco BRL, Cat. No. 18373-027). A cDNA primary strand was prepared from mRNA prepared from *Candida utilis* by using Rneasy Mini Kit (QIAGEN, Cat. No. 74104), and PCR was performed three times. The primers used are shown below.

```
First PCR:
AAG ATA TAC CCA TTG GAT GG    (SEQ ID NO: 12)
and AUAP primer attached
to the 3' RACE Kit Second PCR:
TCA GAT CTT GGT AAA GAG GC    (SEQ ID NO: 13)
and AUAP primer attached
to the 3' RACE Kit Third PCR:
AGA CTG GCA TTT GAG TCT CC    (SEQ ID NO: 14)
and AUAP primer attached
to the 3' RACE Kit
```

PCR was performed by using KOD Dash (TOYOBO, Code LDP-101) according to the manufacturer's instruction with the conditions of a reaction at 94° C. for 2 minutes, followed by reactions at 94° C. for 1 minute, 50° C. for 30 seconds and 74° C. for 40 seconds repeated for 30 cycles.

The PCR product was ligated to the pGEM-T Easy vector and used to transform *Escherichia coli*. The nucleotide sequence of the insert included in the obtained transformant was analyzed to obtain information of a gene fragment expected to encode glutathione synthetase of *Candida utilis*.

Primers (GGT TCT AAG AAG ATT CAG CA, SEQ ID NO: 15) and CCC TCG GAA AAG GAG ACG AAG G, SEQ ID NO: 16) were designed based on the information found by the above operations, PCR was performed by using chromosomal DNA recovered from the *Candida utilis* ATCC15239 strain as a template, and the nucleotide sequence of the amplification product was determined. PCR was performed by using Pyrobest (Takara Shuzo, Code R0005A) according to the manufacturer's instruction with the conditions of a reaction at 98° C. for 2 minutes, followed by reactions at 98° C. for 20 seconds, 55° C. for 30 seconds and 72° C. for 2 minutes repeated for 40 cycles. The result is shown in SEQ ID NO: 17. The amino acid sequence of glutathione synthetase expected to be encoded by this nucleotide sequence is shown in SEQ ID NO: 18.

<2> Production of Gene Disruption Cassette for Glutathione Synthetase of *Candida utilis*

PCR was performed by using chromosomal DNA recovered from *Candida utilis* ATCC15239 as a template and the aforementioned primers of SEQ ID NOS: 15 and 16. PCR was performed by using Pyrobest (Takara Shuzo) according to the manufacturer's instruction with the conditions of a reaction at 98° C. for 2 minutes, followed by reactions at 98° C. for 20 seconds, 55° C. for 30 seconds and 72° C. for 2 minutes repeated for 40 cycles.

The amplification product was purified by using QIA Quick PCR Purification Kit (QIAGEN, Cat. No. 28106), and the purification product was added with adenine at the termini and ligated to the pGEM-T Easy vector. The addition of adenine was performed by using AmpliTaq (ABI, Code N808-0161) and 2.5 mM dATP instead of dNTP by a reaction at 72° C. for 10 minutes. Subsequently, nucleotide sequences at two sites in the cloned fragment were replaced by site-directed recombination using QuikChange Site-Directed Mutagenesis Kit (STRATAGENE, Catalog #200518) to introduce HindIII and KpnI digestion sites and thereby obtain a CGSH2Ctermi/pGEMT-Easy vector. The primers used for the site-directed recombination are shown below.

[First Introduction of Mutation (Introduction of HindIII Digestion Site)]

```
GAA GCC TCA GCA TGA AGC TTG TGG    (SEQ ID NO: 19)
TAA TAA CAT TTA C

G TAA ATG TTA TTA CCA CAA GCT      (SEQ ID NO: 20)
TCA TGC TGA GGC TTC
```

[Second Introduction of Mutation (Introduction of KpnI Digestion Site)]

```
CGA CCA ATC GAC TGG TAC CGT TAT    (SEQ ID NO: 21)
CAA AAA CTC TG

CA GAG TTT TTG ATA ACG GTA CCA     (SEQ ID NO: 22)
GTC GAT TGG TCG
```

Further, PCR was performed by using chromosomal DNA recovered from *Candida utilis* ATCC15239 as a template and the following primers to amplify a fragment including the URA3 gene. PCR was performed by using KOD Dash (TOYOBO, Code LDP-101) according to the manufacturer's instruction with the conditions of a reaction at 94° C. for 2 minutes, followed by reactions at 94° C. for 1 minute, 54° C. for 30 seconds and 74° C. for 40 seconds repeated for 30 cycles.

```
CCC AAG CTT CTC TAC TTG CTT CTG    (SEQ ID NO: 23)
CTC AAC

GCA GGT ACC AAC TTC CGA AAA CAG    (SEQ ID NO: 24)
TAA TGA AC
```

The amplification product was introduced into the pGEMT-Easy vector to obtain a CURA3/pGEMT-Easy vector. The CGSH2Ctermi/pGEMT-Easy vector and the CURA3/pGEMT-Easy vector were each digested with HindIII and KpnI. A fragment including CGSH2 and a main part of pGEMT-Easy was recovered from the CGSH2Ctermi/pGEMT-Easy vector, and a fragment including CURA3 was recovered from the CURA3/pGEMT-Easy vector. These recovered fragments were ligated to each other and used to transform *Escherichia coli* JM109. Thus, a CURA3ΔCGSH2/pGEMT-Easy vector was produced.

PCR amplification was performed by using the CURA3ΔCGSH2/pGEMT-Easy vector digested with a restriction enzyme NotI as a template and the primers of SEQ ID NOS: 15 and 16. Thus, a gene disruption cassette for glutathione synthetase of *Candida utilis* was produced (FIGS. 1 and 2).

<3> Acquisition of Uracil Auxotrophic *Candida utilis* ATCC15239ura- Strain

ATCC15239ura- strain, a uracil-auxotrophic strain derived from ATCC15239, was obtained in a conventional manner (the technique of Luis et al., refer to FEMS Microbiology Letters 165, 335-340 (1998)). Since the ATCC15239ura- strain was complemented by the URA3 gene as described later, this strain is expected to be a ura3 mutant.

<4> Acquisition of γ-Glutamylcysteine Producing Yeast (ATCC15239Δgsh2 Strain) Derived from *Candida utilis*

First, the ATCC15239ura- strain was cultured overnight at 30° C. in a YPD test tube medium. The culture product was inoculated in a YPD flask medium (500-ml Sakaguchi flask, 50 ml filled) and cultured at 30° C. with shaking. The cells were collected in the logarithmic growth phase and washed three times with a 1 M sorbitol solution cooled to 4° C. The washed cells were suspended in a cooled 1 M sorbitol solution. The suspension was added with 50 μl (2 μg) of the glutathione synthetase gene disruption cassette, mixed well in a 0.2 cm cuvette and subjected to electroporation by using Gene Pulser System (BioRad) with impedance of 200 U, capacitance of 125 μF and set voltage of 1.5 kV. In an amount of 1 ml of cooled 1 M sorbitol was poured into the cuvette, and the cuvette was cooled on ice for 10 minutes. The cell suspension was spread over an SD plate and cultured at 30° C. as stationary culture.

The strains grown on the plate were replicated on an SD plate and an SD plate containing 10 mM methylglyoxal and cultured at 30° C. as stationery culture. Seven strains showing susceptibility to methylglyoxal were selected. These 7 strains were each cultured overnight at 30° C. in a YPD test tube medium with shaking. The culture broth was inoculated in an amount of 2% to an SD medium (500-ml Sakaguchi flask, 50 ml filled) and cultured at 30° C. with shaking. The cells in the logarithmic growth phase were collected and washed twice with sterilized water. The washed cells were extracted with hot water at 70° C. for 10 minutes, and γ-glutamylcysteine extracted from the yeast cells was isolated and quantified by HPLC. Further, after placing the washed yeast cells contained in a certain amount of medium on filter paper and heated at 105° C. for 4 hours, the weight of the remaining cells was measured as the dry cell weight of the yeast. Thus, the ATCC15239Δgsh2 strain was obtained as a *Candida utilis* strain containing 1% or more of γ-glutamylcysteine based on dry yeast cells.

The ATCC15239Δgsh2 strain was inoculated in an SD medium and cultured at 30° C. for 2 days with shaking. The culture was inoculated at a concentration of 2% in an SD medium and cultured at 30° C. with shaking. The γ-glutamylcysteine contents measured were 1.08% and 1.12% after 7 hours and 9 hours, respectively. Glutathione content was below the detection limit.

<5> Measurement of Glutathione Synthetase Activity of ATCC15239Δgsh2 Strain

The ATCC 15239Δgsh2 strain was inoculated in a YPD medium and cultured at 30° C. with shaking. The culture was inoculated at a concentration of 2% in an SD medium (2-L finned conical flask, filled 400 ml) and cultured at 30° C. with shaking. Cells in the logarithmic growth phase were collected and washed twice with 1 M sorbitol cooled to 4° C. The washed cells were suspended in 0.5 ml of 10 mM Tris-HCl buffer (pH 7.5) containing 0.1 mM phenylmethanesulfonyl fluoride (PMSF). The suspension was added with glass beads (GLASS BEADS 425-600 Microns Acid-Washed (SIGMA, Code G-8772)), and the cells were disrupted by using BEAD-BEATER (WAKENYAKU). The disruption of cells was confirmed microscopically. Then, 1 ml of the aforementioned buffer was added, and the glass beads and cell debris were removed by centrifugation. Thus, a crude cell extract was obtained. The crude cell extract was purified by using ULTRAFREE-15 Biomax 10 (MILLIPORE, Cat. No. UFV2BGC40) to obtain an enzyme solution. The protein content in the obtained enzyme solution was quantified by the Bradford method. Color development was attained by using Protein Assay CBB Solution (Nakarai, Code 29449-15), and absorbance at 595 nm was measured. A standard curve was created by using Albumin Standard (PIERCE, No. 23210).

The glutathione synthetase activity in the enzyme solution obtained as described above was measured according to the method of Gushima et al. (T. Gushima et al., J. Appl. Biochem., 5, 210 (1983)) as follows.

| [Reaction mixture] | |
|---|---|
| 100 mM γ-glutamyicysteine | 100 μl |
| 100 mM MgCl$_2$ | 100 μl |
| 50 mM ATP | 100 μl |
| 100 mM Gly | 100 μl |
| 1 M Tris-HCl (pH 8.0) | 85.5 μl |
| 160 mM PEP | 12.5 μl |
| 1 mg/ml PK | 2 μl |
| Enzyme solution (1 to 10 mg protein) | |
| Purified water | |
| Total | 2 ml |

PEP: phosphoenolpyruvic acid (SIGMA, Code P-7127)
PK: pyruvate kinase (SIGMA, Code P-1903)

The reaction mixture having the above composition was allowed to react at 30° C. for 0 to 2 hours in the presence of the enzyme in an amount of 1 to 10 mg protein. The reaction mixture was added with ⅕ equivalent of methacrylic acid to terminate the reaction and then adjusted to pH 8.0, and the amount of the produced GSH was determined. The enzymatic activity at this time was below the detection limit and was not detected.

Subsequently, the glutathione synthetase activity of the ATCC15239 strain, which is a parent strain of the ATCC15239Δgsh2 strain, was similarly measured. As a result, the glutathione synthetase activity of the ATCC15239 strain was 0.383 μmol-GSH/mg protein/hour.

EXAMPLE 2

Acquisition of γ-glutamylcysteine Synthetase Gene

<1> Acquisition of γ-glutamylcysteine Synthetase Gene Homologue

The following sequences showing high homology were selected from the amino acid sequences of γ-glutamylcysteine synthetases of *Saccharomyces cerevisiae* and *Schizosaccharomyces pombe* (Ohtake et al., Yeast, 7 (9): 953-961 (December, 1991); Mutoh et al., J. Biochem. (Tokyo), 117 (2): 283-288 (February, 1995)).

```
(i)     MGFGMG      (SEQ ID NO: 25)

(ii)    GWRVEFR     (SEQ ID NO: 26)
```

Degenerated primers were designed based on each amino acid sequence, and degenerated PCR was performed. A primer F1 (ATG GGN TTY GGN ATG GG, SEQ ID NO: 27) was designed as a primer corresponding to the region of (i), and a primer R1 (RAA YTC NAC NCK CCA, SEQ ID NO: 28) was designed as a primer corresponding to the region of (ii). PCR was performed by using KOD Dash (TOYOBO) as DNA polymerase according to the manufacturer's instruction with the conditions of a reaction at 94° C. for 3 minutes, followed by reactions at 94° C. for 1 minute, 52° C. for 1 minute and 74° C. for 1 minute repeated for 30 cycles.

The PCR product was subjected to agarose gel electrophoresis, a region corresponding to the expected size of about 700 bp was excised, and DNA was recovered from the gel by using MagExtractor (TOYOBO, Code NPK-601).

Further, nested PCR was performed by using this recovered DNA as a template. PCR was performed in the same manner as described above. The amplification product was subjected to agarose gel electrophoresis and then stained by using an ethidium bromide solution, a region corresponding to about 700 bp was excised, and DNA was recovered from the gel by using MagExtractor. The recovered DNA was ligated to the pGEM-T Easy vector by using DNA Ligation Kit Ver. 2 (Takara Shuzo) and used to transform *Escherichia coli* JM109 competent cells. Among the obtained transformants, one was obtained as a transformant considered to contain a gene fragment expected to encode γ-glutamylcysteine synthetase of *Candida utilis*. The nucleotide sequence of the insert included in the transformant was determined in a conventional manner.

3' RACE was performed based on the nucleotide sequence determined as described above by using 3' RACE System for Rapid Amplification of cDNA Ends (GIBCO BRL). A cDNA primary strand was synthesized from mRNA prepared from *Candida utilis* by using Rneasy Mini Kit, and PCR was performed 3 times.

The primers used are shown below.

```
First PCR:
TGA ACA GAG CTC GTT ACC TC    (SEQ ID NO: 29)
and AUAP primer attached
to the 3' RACE Kit Second PCR:
TCA TGG GCT AAT TTT GCA CC    (SEQ ID NO: 30)
and AUAP primer attached
to the 3' RACE Kit Third PCR:
TTC CTA GCA TTG ACG GCA GC    (SEQ ID NO: 31)
and AUAP primer attached
to the 3' RACE Kit
```

PCR was performed by using KOD Dash according to the manufacturer's instruction with the conditions of a reaction at 94° C. for 2 minutes, followed by reactions at 94° C. for 1 minute, 50° C. for 30 seconds and 74° C. for 40 seconds repeated for 30 cycles. The PCR product was ligated to the pGEM-T Easy vector and used to transform *Escherichia coli*. The nucleotide sequence of the insert included in the transformant was analyzed to obtain information about the gene fragment expected to contain the γ-glutamylcysteine synthetase gene of *Candida utilis*.

Subsequently, 5' RACE was performed based on the nucleotide sequences previously elucidated. The kit used was 5' RACE System for Rapid Amplification of cDNA Ends Reagent Assembly Version 2.0 (GIBCO BRL).

The primer used for RT (reverse transcription) for preparing a cDNA primary strand is shown below.

```
AGC ACC AGA AAT GAC GTT C    (SEQ ID NO: 32)
```

PCR was performed 3 times by using the cDNA library constructed according to the manufacturer's instruction and the following primers. PCR was performed by using KOD Dash according to the manufacturer's instruction with the conditions of a reaction at 94° C. for 2 minutes, followed by reactions at 94° C. for 1 minute, 50° C. for 30 seconds and 74° C. for 40 seconds repeated for 30 cycles.

The primers used are shown below.

```
First PCR:
CCA TCT GAC GAC ATC CTG CTG    (SEQ ID NO: 33)
and AUAP primer attached
to the kit Second PCR:
GTC AGC TAA GTG GCC TTT G      (SEQ ID NO: 34)
and AUAP primer attached
to the kit Third PCR:
CAC TGG CGC TGC TGC CGT C      (SEQ ID NO: 35)
and AUAP primer attached
to the kit
```

The PCR product was ligated to the pGEM-T Easy vector and used to transform *Escherichia coli*. The nucleotide sequence of the insert included in the transformant was analyzed to obtain information about the gene fragment expected to contain the γ-glutamylcysteine synthetase gene of *Candida utilis*. Based on homologies with those of other organisms, it was considered that the full length had not been cloned, and 5' RACE was further performed.

The primer used for RT to prepare a cDNA primary strand is shown below.

```
TGA TCT TCT GCT GTT CAT GTT    (SEQ ID NO: 36)
```

PCR was performed 3 times by using the cDNA library constructed according to the manufacturer's instruction.

The primers used are shown below.

```
First PCR:
CTC CAC GTA CAA GTA GTT CTC    (SEQ ID NO: 37)
and
AUAP primer attached to the kit Second PCR:
CAG CGA ATC ACC GTT GTA CGG    (SEQ ID NO: 38)
and
AUAP primer attached to the kit Third PCR:
AGC CAG CGG TGT CGC CTC        (SEQ ID NO: 39)
and
AUAP primer attached to the kit
```

The PCR product was ligated to the pGEM-T Easy vector and used to transform *Escherichia coli*. The nucleotide sequence of the insert included in the transformant was analyzed to obtain information about the gene fragment expected to contain the γ-glutamylcysteine synthetase gene of *Candida utilis*.

Primers were designed based on the information obtained as described above, PCR was performed, and the nucleotide sequence of the amplification product was determined. PCR was performed by using Pyrobest (Takara Shuzo) according to the manufacturer's instruction with the conditions of a reaction at 98° C. for 2 minutes, followed by reactions at 98° C. for 20 seconds, 55° C. for 30 seconds and 72° C. for 2 minutes repeated for 40 cycles.

The primers used are shown below.

```
Primer F2:
GGG TTT GTT GTC TAT CGG CTT AAG    (SEQ ID NO: 40)

Primer R2:
AGC TGT CTT GGT CGT CAT ATC CAT    (SEQ ID NO: 41)
```

The nucleotide sequence of the PCR product amplified as described above was determined in a conventional manner. The result is shown in SEQ ID NO: 42. Further, the amino acid sequence of γ-glutamylcysteine synthetase expected to be encoded by this nucleotide sequence is shown in SEQ ID NO: 43. Thus, a homologue of the γ-glutamylcysteine synthetase gene of *Candida utilis* was obtained.

EXAMPLE 3

Expression of γ-glutamylcysteine Synthetase Gene in *Saccharomyces cerevisiae*

<1> *Saccharomyces cerevisiae* Having Reduced Glutathione Synthetase Activity

As *Saccharomyces cerevisiae* having a reduced glutathione synthetase activity, the *Saccharomyces cerevisiae* Nα3 strain described in International Patent Publication WO01/90310 was used.

The Nα3 strain is a strain constructed as an attenuated glutathione synthetase gene-substituted strain by using the Nα1 strain (described in International Patent Publication WO01/90310) as a parent strain, which is a haploid uracil-auxotrophic strain of *Saccharomyces cerevisiae*.

<2> Acquisition of *Saccharomyces cerevisiae* Having Reduced γ-glutamylcysteine Synthetase Activity (1) Production of GSH1 Gene Substitution Cassette First, the fragment ranging from the mid-stream region to the end region of the γ-glutamylcysteine synthetase gene (SEQ ID NO: 44) was amplified by PCR using chromosomal DNA of the aforementioned Nα1 strain as a template. PCR was performed by using KOD Dash (TOYOBO) and a reaction mixture having the following composition according to the manufacturer's instruction with the conditions of a reaction at 94° C. for 1 minute, followed by reactions at 94° C. for 30 seconds, 60° C. for 40 seconds and 74° C. for 1 minute repeated for 30 cycles. As primers, GF1 (gtg gac gac cgt act ccg aag, SEQ ID NO: 46) and GR1 (acc caa atc gat aat gtc aac, SEQ ID NO: 47) were used.

The GSH1 gene fragment amplified as described above was ligated to the plasmid pGEM-T Easy (Promega) according to the manufacturer's instruction to obtain GSH1dash/pGEM.

Subsequently, by site-directed mutagenesis, codons in the γ-glutamylcysteine synthetase gene (SEQ ID NO: 44) included in GSH1dash/pGEM corresponding to amino acids of the 372nd and 373rd positions, serine and lysine, in γ-glutamylcysteine synthetase (SEQ ID NO: 45) encoded by this gene were replaced with a stop codon. This operation was performed by using Quick Change Site-Directed Mutagenesis Kit (STRATAGENE) according to the protocol of the manufacturer. As primers, QCF1 (ctt ttc ttg ggt ggg tag taa ttt ttc aat agg act, SEQ ID NO: 48) and QCR1 (agt cct att gaa aaa tta cta ccc acc caa gaa aag, SEQ ID NO: 49) were used. Thus, the plasmid GSH1Mdash/pGEM was produced.

The γ-glutamylcysteine synthetase introduced with a mutation as described above has a weak enzymatic activity (attenuated glutathione synthetase, International Patent Publication WO01/90310).

Subsequently, the plasmids pYES2dash (a plasmid obtained by eliminating 2μ ori from the plasmid pYES2 (Invitrogen)) described in International Patent Publication WO01/90310 and the aforementioned GSH1Mdash/pGEM were both digested with restriction enzymes SacI and SphI. A fragment including the URA3 gene was excised from pYES2dash, a region including a partial gene sequence of γ-glutamylcysteine synthetase was excised from GSH1Mdash/pGEM, and these were ligated to each other to prepare a plasmid GSH1Mdash/pYES2dash. GSH1Mdash/pYES2dash was digested with a restriction enzyme BbeI to obtain a gene substitution cassette (FIG. 3).

(2) Construction of γ-glutamylcysteine Synthetase Gene-substituted Strain

Gene substitution of the γ-glutamylcysteine synthetase gene in the Nα1 strain was performed by using the gene substitution cassette produced as described above. The Nα1 strain was precultured, and the culture was subcultured in 50 ml of YPD medium until the cells reached the logarithmic growth phase. The cultured cells were suspended in 1 M sorbitol, mixed with the gene substitution cassette and transformed by electroporation. The transformant strains were cultured on an SD plate containing 1 mM glutathione, and grown strains were selected. It was confirmed by PCR that the gene substitution cassette had been incorporated into the chromosome at the target position, and the obtained strain was designated as an Nα4 intermediate. Subsequently, the following operation was performed to leave only the mutant γ-glutamylcysteine synthetase gene on the chromosome. The Nα4 intermediate was cultured in a YPD medium containing 1 mM glutathione, and the culture product was inoculated on an SDFOA plate containing 1 mM glutathione. The glutathione synthetase gene of a strain grown on the plate was sequenced to confirm that the sequence at the target site was correctly substituted, and thus the Nα4 strain was obtained (FIG. 4).

(3) Confirmation of Attenuation of γ-glutamylcysteine Synthetase Activity in Nα4 Strain Subsequently, whether the γ-glutamylcysteine synthetase activity of the Nα4 strain obtained as described above was attenuated or not was examined. Ohtake et al. measured the γ-glutamylcysteine synthetase activity of the YH1 strain obtained from the *Saccharomyces cerevisiae* YNN27 strain by mutagenesis treatment (Agric. Biol. Chem., 54 (12): 3145-3150 (1990)). The activity was measured according to this method. As a result, the γ-glutamylcysteine synthetase activity of the Nα4 strain was below the detection limit. Then, the Nα4 strain was cultured in an SD medium, and the contents of γ-glutamylcysteine and glutathione in the cells in the logarithmic growth phase were measured. However, γ-glutamylcysteine was not detected, and the concentration of glutathione was 0.01%. Further, since the Nα4 strain exhibited susceptibility to 2 mM methylglyoxal, it was confirmed that the γ-glutamylcysteine synthetase gene had been substituted as in the case of the YH1 strain.

<2> Construction of Expression Vector of γ-glutamylcysteine Synthetase Homologue Derived from *Candida utilis*

PCR was performed by using chromosomal DNA of *Candida utilis* as a template to amplify the ORF region of the γ-glutamylcysteine synthetase gene homologue of *Candida utilis*. PCR was performed by using Pyrobest (Takara Shuzo)

according to the manufacturer's instruction with the conditions of a reaction at 98° C. for 2 minutes, followed by reactions at 98° C. for 20 seconds, 55° C. for 30 seconds and 72° C. for 2 minutes repeated for 40 cycles. PCR was performed by using a N-terminus primer CGSH1F1 (GAG TAC GGT ACC ATG GGG CTG CTA TCA TTA GGG AC, SEQ ID NO: 50), to which a KpnI digestion site was added, and a C-terminus primer CGSH1R1 (CCC TTA TCT AGA TTA AGC CTT TGG GTT GTT TAT C, SEQ ID NO: 51), to which a XbaI digestion site was added, under the above condition, and the amplification product was purified by using QIAquick PCR purification Kit. The purified PCR product and the pAUR123 vector (Takara Shuzo) were digested with restriction enzymes KpnI and XbaI, then ligated to each other and used to transform *Escherichia coli* JM109 competent cells. Thus, the CGSH1/pAUR123 vector was produced. Subsequently, the CGSH1/pAUR123 vector and the pYES2 vector were digested with a restriction enzyme BamHI. A region including ORF of CGSH1 and a promoter derived from the pAUR123 vector was recovered from the CGSH1/pAUR123 vector, ligated to the pYES2 vector of which digested ends were dephosphorylated, and used to transform *Escherichia coli* JM109 competent cells. Thus, the CGSH1/pYES2 vector, an expression vector of the γ-glutamylcysteine synthetase homologue of *Candida utilis*, was produced (FIG. 5).

<3> Complementation Test

Subsequently, transformants were obtained by introducing the CGSH1/pYES2 vector into the Nα3 strain and the Nα4 strain. The Nα3 strain or the Nα4 strain was precultured and subcultured in 50 ml of a liquid medium (YPD medium containing 1 mM glutathione) until the cells reached the logarithmic growth phase. The cultured cells were suspended in 1 M sorbitol, mixed with the CGSH1/pYES2 vector and transformed by electroporation. The transformed strains were cultured on an SD plate containing 1 mM glutathione, and grown strains were selected. The Nα3 strain and the Nα4 strain showed uracil auxotrophy and could grow in the SD medium only when the CGSH1/pYES2 vector was included. It was confirmed that the obtained transformants included the CGSH1/pYES2 vector in a conventional manner.

Thus, transformants, the Nα3/CGSH1 and Nα4/CGSH1 strains, were obtained. Nα3/CGSH1 showed susceptibility to 2 mM methylglyoxal, whereas the Nα4/CGSH1 strain did not show susceptibility to 2 mM methylglyoxal. Further, when cultured in the SD medium, the Nα3/CGSH1 strain contained almost no glutathione in the logarithmic growth phase, whereas the Nα4/CGSH1 strain contained 0.4% glutathione. The Nα3 strain had a reduced glutathione synthesis ability due to a mutation occurred in glutathione synthetase of *Saccharomyces cerevisiae*, whereas the Nα4 strain had a reduced glutathione synthesis ability due a mutation occurred in γ-glutamylcysteine synthetase of *Saccharomyces cerevisiae*. Thus, it was demonstrated that CGSH1 complemented γ-glutamylcysteine synthetase of *Saccharomyces cerevisiae*.

INDUSTRIAL APPLICABILITY

The present invention provides *Candida utilis* having a high content of γ-glutamylcysteine. Yeast extract that can be used for improving flavor and taste of food and so forth can be produced at a low cost by using the *Candida utilis* of the present invention.

What is claimed is:

1. An isolated *Candida utilis* which is transformed with a gene encoding γ-glutamylcysteine synthetase from *Candida utilis* and contains 1% by weight or more of γ-glutamylcysteine per dry cells in its logarithmic growth phase when cultured in a minimal medium, wherein said γ-glutamylcysteine synthetase is:
   (A) a protein which has the amino acid sequence of SEQ ID NO: 43; or
   (B) a protein variant having the amino acid sequence of SEQ ID NO: 43 modified by substitution, deletion, insertion or addition of one to eight amino acids, and has γ-glutamylcysteine synthetase activity.

2. The *Candida utilis* according to claim 1, wherein the minimal medium is SD medium.

3. The *Candida utilis* according to claim 1, wherein a gene encoding glutathione synthetase is disrupted so that intracellular glutathione synthetase activity is reduced.

4. The *Candida utilis* according to claim 3, which shows glutathione synthetase activity of 0.005 μmol GSH/mg protein/hour or lower.

5. A food or drink comprising a culture obtained by culturing the *Candida utilis* according to claim 1 under suitable conditions.

6. The food or drink according to claim 5, which is a fermented food seasoning.

7. A method for producing a food or drink containing γ-glutamylcysteine or cysteine, which comprises:
   (a) culturing the *Candida utilis* according to claim 1 under suitable conditions;
   (b) optionally heat treating the *Candida utilis* culture of step (a); and
   (c) mixing the culture of (a) or (b), or a fraction thereof containing γ-glutamylcysteine or cysteine, with a food or drink raw material.

8. An isolated DNA which encodes a protein defined in the following (A) or (B):
   (A) a protein which has the amino acid sequence of SEQ ID NO: 43; or
   (B) a protein variant having the amino acid sequence of SEQ ID NO: 43 modified by substitution, deletion, insertion or addition of one to eight amino acids, and has γ-glutamylcysteine synthetase activity.

9. The DNA according to claim 8, which comprises the nucleotide sequence of the nucleotide numbers from 110 to 2101 of SEQ ID NO: 42.

* * * * *

SEQUENCE LISTING

```
<160> NUMBER OF SEQ ID NOS: 51

<210> SEQ ID NO 1
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 1

Gln Glu Val Ala Val Val Tyr Tyr Arg
1               5

<210> SEQ ID NO 2
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 2

Gly Ser Lys Lys Ile Gln Gln
1               5

<210> SEQ ID NO 3
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 3
```

```
Val Leu Lys Pro Gln Arg Glu Gly Gly Asn Asn
1               5                   10

<210> SEQ ID NO 4
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 4

Ile Ser Glu Leu Gly Ile Tyr Gly
1               5

<210> SEQ ID NO 5
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 5

Gly Gly Val Ala Ala Gly Phe
1               5

<210> SEQ ID NO 6
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 6

Gly Ser Lys Lys Ile Gln Gln
1               5

<210> SEQ ID NO 7
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 7

Glu Gly Gly Gly Asn Asn
1               5

<210> SEQ ID NO 8
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 8

Pro Gln Arg Glu Gly Gly Gly
1               5

<210> SEQ ID NO 9
<211> LENGTH: 20
<212> TYPE: DNA
<213> ORGANISM: Artificial Sequence
<220> FEATURE:
<223> OTHER INFORMATION: Synthetic DNA

<400> SEQUENCE: 9
```
ggttcyaaga agatycarca                    20

<210> SEQ ID NO 10
<211> LENGTH: 20
<212> TYPE: DNA
<213> ORGANISM: Artificial Sequence
<220> FEATURE:
<223> OTHER INFORMATION: Synthetic DNA

<400> SEQUENCE: 10
ccaccaccyt ctctytgtgg                    20

<210> SEQ ID NO 11
<211> LENGTH: 18
<212> TYPE: DNA
<213> ORGANISM: Artificial Sequence
<220> FEATURE:
<223> OTHER INFORMATION: Synthetic DNA

<400> SEQUENCE: 11
gttgttacca ccaccytc                      18

<210> SEQ ID NO 12
<211> LENGTH: 20
<212> TYPE: DNA
<213> ORGANISM: Artificial Sequence
<220> FEATURE:
<223> OTHER INFORMATION: Synthetic DNA

<400> SEQUENCE: 12
aagatatacc cattggatgg                    20

<210> SEQ ID NO 13
<211> LENGTH: 20
<212> TYPE: DNA
<213> ORGANISM: Artificial Sequence
<220> FEATURE:
<223> OTHER INFORMATION: Synthetic DNA

<400> SEQUENCE: 13
tcagatcttg gtaaagaggc                    20

<210> SEQ ID NO 14
<211> LENGTH: 20
<212> TYPE: DNA
<213> ORGANISM: Artificial Sequence
<220> FEATURE:
<223> OTHER INFORMATION: Synthetic DNA

<400> SEQUENCE: 14
agactggcat ttgagtctcc                    20

<210> SEQ ID NO 15
<211> LENGTH: 20
<212> TYPE: DNA
<213> ORGANISM: Artificial Sequence
<220> FEATURE:
<223> OTHER INFORMATION: Synthetic DNA

<400> SEQUENCE: 15
ggttctaaga agattcagca                    20

<210> SEQ ID NO 16
<211> LENGTH: 22
<212> TYPE: DNA
<213> ORGANISM: Artificial Sequence
<220> FEATURE:
<223> OTHER INFORMATION: Synthetic DNA

<400> SEQUENCE: 16
ccctcggaaa aggagacgaa gg                                             22

<210> SEQ ID NO 17
<211> LENGTH: 573
<212> TYPE: DNA
<213> ORGANISM: Candida utilis
<220> FEATURE:
<221> NAME/KEY: CDS
<222> LOCATION: (1)..(510)
<223> OTHER INFORMATION:

<400> SEQUENCE: 17

```
ggt tct aag aag att cag caa atc ttg acg gat gag aag gta ctc tcc       48
Gly Ser Lys Lys Ile Gln Gln Ile Leu Thr Asp Glu Lys Val Leu Ser
1               5                   10                  15 aag ttt att aag tct gat gtc tcc gag ttg gtg tca aca ttt gtc aag       96
Lys Phe Ile Lys Ser Asp Val Ser Glu Leu Val Ser Thr Phe Val Lys
                20                  25                  30 ata tac cca ttg gat ggt tca gat ctt ggt aaa gag gct aaa aga ctg      144
Ile Tyr Pro Leu Asp Gly Ser Asp Leu Gly Lys Glu Ala Lys Arg Leu
            35                  40                  45 gca ttt gag tct cca gag gag tac gtg ttg aag cct cag cat gaa ggt      192
Ala Phe Glu Ser Pro Glu Glu Tyr Val Leu Lys Pro Gln His Glu Gly
        50                  55                  60 ggt ggt aat aac att tac aaa gaa gat ata cct ggt ttc tta aga tct      240
Gly Gly Asn Asn Ile Tyr Lys Glu Asp Ile Pro Gly Phe Leu Arg Ser
65                  70                  75                  80 att cca gaa gat gaa tgg caa gga tac att cta atg caa ttg atc cat      288
Ile Pro Glu Asp Glu Trp Gln Gly Tyr Ile Leu Met Gln Leu Ile His
                85                  90                  95 cca cct ctg aat aag aat aaa ctc gtc cgt gag ggt gag gta ttt aca      336
Pro Pro Leu Asn Lys Asn Lys Leu Val Arg Glu Gly Glu Val Phe Thr
                100                 105                 110 gat gag ata gtt tct gag ctt ggc cgt ttc ggc acc atc tta ttc gac      384
Asp Glu Ile Val Ser Glu Leu Gly Arg Phe Gly Thr Ile Leu Phe Asp
            115                 120                 125 caa tcg act ggt gag gtt atc aaa aac tct gat gct ggc tgg ttg ttg      432
Gln Ser Thr Gly Glu Val Ile Lys Asn Ser Asp Ala Gly Trp Leu Leu
        130                 135                 140 aga tcg aaa ttc tca agc tcc aac gaa ggt ggt gtt gct gca ggg ttt      480
Arg Ser Lys Phe Ser Ser Ser Asn Glu Gly Gly Val Ala Ala Gly Phe
145                 150                 155                 160 gga tgt gtt gat ggt gtt gct ctc caa tag atggagccgc atttagatat        530
Gly Cys Val Asp Gly Val Ala Leu Gln
                165 ccacctcacg aattagaatt ccttcgtctc cttttccgag ggc                     573
```

<210> SEQ ID NO 18
<211> LENGTH: 169
<212> TYPE: PRT
<213> ORGANISM: Candida utilis

<400> SEQUENCE: 18

```
Gly Ser Lys Lys Ile Gln Gln Ile Leu Thr Asp Glu Lys Val Leu Ser
1               5                   10                  15

Lys Phe Ile Lys Ser Asp Val Ser Glu Leu Val Ser Thr Phe Val Lys
                20                  25                  30
```

```
Ile Tyr Pro Leu Asp Gly Ser Asp Leu Gly Lys Glu Ala Lys Arg Leu
            35                  40                  45
Ala Phe Glu Ser Pro Glu Tyr Val Leu Lys Pro Gln His Glu Gly
 50                  55                  60
Gly Gly Asn Asn Ile Tyr Lys Glu Asp Ile Pro Gly Phe Leu Arg Ser
 65                  70                  75                  80
Ile Pro Glu Asp Glu Trp Gln Gly Tyr Ile Leu Met Gln Leu Ile His
                 85                  90                  95
Pro Pro Leu Asn Lys Asn Lys Leu Val Arg Glu Gly Glu Val Phe Thr
                100                 105                 110
Asp Glu Ile Val Ser Glu Leu Gly Arg Phe Gly Thr Ile Leu Phe Asp
            115                 120                 125
Gln Ser Thr Gly Glu Val Ile Lys Asn Ser Asp Ala Gly Trp Leu Leu
130                 135                 140
Arg Ser Lys Phe Ser Ser Asn Glu Gly Gly Val Ala Ala Gly Phe
145                 150                 155                 160
Gly Cys Val Asp Gly Val Ala Leu Gln
                165
```

<210> SEQ ID NO 19
<211> LENGTH: 37
<212> TYPE: DNA
<213> ORGANISM: Artificial Sequence
<220> FEATURE:
<223> OTHER INFORMATION: Synthetic DNA

<400> SEQUENCE: 19
gaagcctcag catgaagctt gtggtaataa catttac                37

<210> SEQ ID NO 20
<211> LENGTH: 37
<212> TYPE: DNA
<213> ORGANISM: Artificial Sequence
<220> FEATURE:
<223> OTHER INFORMATION: Synthetic DNA

<400> SEQUENCE: 20
gtaaatgtta ttaccacaag cttcatgctg aggcttc                37

<210> SEQ ID NO 21
<211> LENGTH: 35
<212> TYPE: DNA
<213> ORGANISM: Artificial Sequence
<220> FEATURE:
<223> OTHER INFORMATION: Synthetic DNA

<400> SEQUENCE: 21
cgaccaatcg actggtaccg ttatcaaaaa ctctg                35

<210> SEQ ID NO 22
<211> LENGTH: 35
<212> TYPE: DNA
<213> ORGANISM: Artificial Sequence
<220> FEATURE:
<223> OTHER INFORMATION: Synthetic DNA

<400> SEQUENCE: 22
cagagttttt gataacggta ccagtcgatt ggtcg                35

<210> SEQ ID NO 23
<211> LENGTH: 30
<212> TYPE: DNA

```
<213> ORGANISM: Artificial Sequence
<220> FEATURE:
<223> OTHER INFORMATION: Synthetic DNA

<400> SEQUENCE: 23
cccaagcttc tctacttgct tctgctcaac                                         30

<210> SEQ ID NO 24
<211> LENGTH: 32
<212> TYPE: DNA
<213> ORGANISM: Artificial Sequence
<220> FEATURE:
<223> OTHER INFORMATION: Synthetic DNA

<400> SEQUENCE: 24
gcaggtacca acttccgaaa acagtaatga ac                                      32

<210> SEQ ID NO 25
<211> LENGTH: 6
<212> TYPE: PRT
<213> ORGANISM: Candida utilis

<400> SEQUENCE: 25

Met Gly Phe Gly Met Gly
1               5

<210> SEQ ID NO 26
<211> LENGTH: 7
<212> TYPE: PRT
<213> ORGANISM: Candida utilis

<400> SEQUENCE: 26

Gly Trp Arg Val Glu Phe Arg
1               5

<210> SEQ ID NO 27
<211> LENGTH: 17
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (6)..(6)
<223> OTHER INFORMATION: n = a, c, g, or t
<220> FEATURE:
<221> NAME/KEY: misc_feature
<222> LOCATION: (12)..(12)
<223> OTHER INFORMATION: n = a, c, g, or t

<400> SEQUENCE: 27
atgggnttyg gnatggg                                                       17

<210> SEQ ID NO 28
<211> LENGTH: 15
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (7)..(7)
<223> OTHER INFORMATION: n = a, c, g, or t
<220> FEATURE:
<221> NAME/KEY: misc_feature
<222> LOCATION: (10)..(10)
<223> OTHER INFORMATION: n = a, c, g, or t

<400> SEQUENCE: 28
```
raaytcnacn ckcca                                                15

<210> SEQ ID NO 29
<211> LENGTH: 20
<212> TYPE: DNA
<213> ORGANISM: Artificial Sequence
<220> FEATURE:
<223> OTHER INFORMATION: Synthetic DNA

<400> SEQUENCE: 29
tgaacagagc tcgttacctc                                           20

<210> SEQ ID NO 30
<211> LENGTH: 20
<212> TYPE: DNA
<213> ORGANISM: Artificial Sequence
<220> FEATURE:
<223> OTHER INFORMATION: Synthetic DNA

<400> SEQUENCE: 30
tcatgggcta attttgcacc                                           20

<210> SEQ ID NO 31
<211> LENGTH: 20
<212> TYPE: DNA
<213> ORGANISM: Artificial Sequence
<220> FEATURE:
<223> OTHER INFORMATION: Synthetic DNA

<400> SEQUENCE: 31
ttcctagcat tgacggcagc                                           20

<210> SEQ ID NO 32
<211> LENGTH: 19
<212> TYPE: DNA
<213> ORGANISM: Artificial Sequence
<220> FEATURE:
<223> OTHER INFORMATION: Synthetic DNA

<400> SEQUENCE: 32
agcaccagaa atgacgttc                                            19

<210> SEQ ID NO 33
<211> LENGTH: 21
<212> TYPE: DNA
<213> ORGANISM: Artificial Sequence
<220> FEATURE:
<223> OTHER INFORMATION: Synthetic DNA

<400> SEQUENCE: 33
ccatctgacg acatcctgct g                                         21

<210> SEQ ID NO 34
<211> LENGTH: 19
<212> TYPE: DNA
<213> ORGANISM: Artificial Sequence
<220> FEATURE:
<223> OTHER INFORMATION: Synthetic DNA

<400> SEQUENCE: 34
gtcagctaag tggcctttg                                            19

<210> SEQ ID NO 35
<211> LENGTH: 19
<212> TYPE: DNA

```
<213> ORGANISM: Artificial Sequence
<220> FEATURE:
<223> OTHER INFORMATION: Synthetic DNA

<400> SEQUENCE: 35
cactggcgct gctgccgtc                                                    19

<210> SEQ ID NO 36
<211> LENGTH: 21
<212> TYPE: DNA
<213> ORGANISM: Artificial Sequence
<220> FEATURE:
<223> OTHER INFORMATION: Synthetic DNA

<400> SEQUENCE: 36
tgatcttctg ctgttcatgt t                                                 21

<210> SEQ ID NO 37
<211> LENGTH: 21
<212> TYPE: DNA
<213> ORGANISM: Artificial Sequence
<220> FEATURE:
<223> OTHER INFORMATION: Synthetic DNA

<400> SEQUENCE: 37
ctccacgtac aagtagttct c                                                 21

<210> SEQ ID NO 38
<211> LENGTH: 21
<212> TYPE: DNA
<213> ORGANISM: Artificial Sequence
<220> FEATURE:
<223> OTHER INFORMATION: Synthetic DNA

<400> SEQUENCE: 38
cagcgaatca ccgttgtacg g                                                 21

<210> SEQ ID NO 39
<211> LENGTH: 18
<212> TYPE: DNA
<213> ORGANISM: Artificial Sequence
<220> FEATURE:
<223> OTHER INFORMATION: Synthetic DNA

<400> SEQUENCE: 39
agccagcggt gtcgcctc                                                     18

<210> SEQ ID NO 40
<211> LENGTH: 24
<212> TYPE: DNA
<213> ORGANISM: Artificial Sequence
<220> FEATURE:
<223> OTHER INFORMATION: Synthetic DNA

<400> SEQUENCE: 40
gggtttgttg tctatcggct taag                                              24

<210> SEQ ID NO 41
<211> LENGTH: 24
<212> TYPE: DNA
<213> ORGANISM: Artificial Sequence
<220> FEATURE:
<223> OTHER INFORMATION: Synthetic DNA

<400> SEQUENCE: 41
agctgtcttg gtcgtcatat ccat                                              24
```

<210> SEQ ID NO 42
<211> LENGTH: 2224
<212> TYPE: DNA
<213> ORGANISM: Candida utilis
<220> FEATURE:
<221> NAME/KEY: CDS
<222> LOCATION: (110)..(2101)
<223> OTHER INFORMATION:

<400> SEQUENCE: 42

```
gggtttgttg tctatcggct taaggtttag tcgggaggaa caagaagcga cacacacagc      60
gaaccgacac acttgggaac ccattgctta agctattgag taccatacg atg ggg ctg     118
                                                      Met Gly Leu
                                                       1 cta tca tta ggg act ccg ctt cct tgg gaa cag aca agg gag tac gcg      166
Leu Ser Leu Gly Thr Pro Leu Pro Trp Glu Gln Thr Arg Glu Tyr Ala
    5                  10                  15 gag cac gtc cgc act gag ggt atc gaa cag ttg atc aag atg ttc aag      214
Glu His Val Arg Thr Glu Gly Ile Glu Gln Leu Ile Lys Met Phe Lys
 20                  25                  30                  35 gct gca tat gca aga acc ggt gat ggc tat cta tgg gga gac gaa gtg      262
Ala Ala Tyr Ala Arg Thr Gly Asp Gly Tyr Leu Trp Gly Asp Glu Val
                 40                  45                  50 gag tat acc ctg gtc aag ttt gat cat ggt cgt ggt ctt gct ctg ttg      310
Glu Tyr Thr Leu Val Lys Phe Asp His Gly Arg Gly Leu Ala Leu Leu
             55                  60                  65 agt atc gat aag gac agc gta ttg gct gat ctc aac gag ggc gga tca      358
Ser Ile Asp Lys Asp Ser Val Leu Ala Asp Leu Asn Glu Gly Gly Ser
         70                  75                  80 ctg gca cag ttg tct gtg gac aat gat ctc aac ttc cac ccg gaa tat      406
Leu Ala Gln Leu Ser Val Asp Asn Asp Leu Asn Phe His Pro Glu Tyr
     85                  90                  95 ggc cgc ttc atg ctg gag gcg aca ccg ctg gct ccg tac aac ggt gat      454
Gly Arg Phe Met Leu Glu Ala Thr Pro Leu Ala Pro Tyr Asn Gly Asp
100                 105                 110                 115 tcg ctg gag aac tac ttg tac gtg gag agg aac atg aac agc aga aga      502
Ser Leu Glu Asn Tyr Leu Tyr Val Glu Arg Asn Met Asn Ser Arg Arg
                120                 125                 130 tca gtg gcg cag act gcg att gct gac ggc acc atc aag ccg ttg acc      550
Ser Val Ala Gln Thr Ala Ile Ala Asp Gly Thr Ile Lys Pro Leu Thr
            135                 140                 145 ata acg gtg tac cca ttg atg ggc atc aac acc ttc acc ttc cca tca      598
Ile Thr Val Tyr Pro Leu Met Gly Ile Asn Thr Phe Thr Phe Pro Ser
        150                 155                 160 gcg gtg gct aac ggc gag gca tca caa tcg ctg ttc tta ccg gat gag      646
Ala Val Ala Asn Gly Glu Ala Ser Gln Ser Leu Phe Leu Pro Asp Glu
    165                 170                 175 atc atc aac aga cat gcg aga ttc cca aca ttg acg gcc aac att cgg      694
Ile Ile Asn Arg His Ala Arg Phe Pro Thr Leu Thr Ala Asn Ile Arg
180                 185                 190                 195 aaa cgc cgt ggt gag aag gtg gcc atc aac gta ccg ctc tac aag gat      742
Lys Arg Arg Gly Glu Lys Val Ala Ile Asn Val Pro Leu Tyr Lys Asp
                200                 205                 210 aca aat acg tta tcc att gac gag tca att cca aag gga cgc tcc ctg      790
Thr Asn Thr Leu Ser Ile Asp Glu Ser Ile Pro Lys Gly Arg Ser Leu
            215                 220                 225 ttc aag cac gac gaa gaa cca gag ctc ggt gca gca ctg cca ggg cat      838
Phe Lys His Asp Glu Glu Pro Glu Leu Gly Ala Ala Leu Pro Gly His
        230                 235                 240
```

| | | |
|---|---|---|
| ata tac atg gac tcc atg gga ttc ggt atg gga tgc tca tgt cta caa<br>Ile Tyr Met Asp Ser Met Gly Phe Gly Met Gly Cys Ser Cys Leu Gln<br>245                      250                      255 | | 886 |
| gta aca gtg caa gca cca aac ttg aac aga gct cgt tac ctc tat gat<br>Val Thr Val Gln Ala Pro Asn Leu Asn Arg Ala Arg Tyr Leu Tyr Asp<br>260                      265                      270                      275 | | 934 |
| tca tgg gct aat ttt gca cca ttg ttc cta gca ttg acg gca gca gcg<br>Ser Trp Ala Asn Phe Ala Pro Leu Phe Leu Ala Leu Thr Ala Ala Ala<br>                      280                      285                      290 | | 982 |
| cca gtg ttc aaa ggc cac tta gct gac cag gat gtc aga tgg aac gtc<br>Pro Val Phe Lys Gly His Leu Ala Asp Gln Asp Val Arg Trp Asn Val<br>              295                      300                      305 | | 1030 |
| att tct ggt gct gtt gat gat cgt act gcc tac gag cgt gat gtt aag<br>Ile Ser Gly Ala Val Asp Asp Arg Thr Ala Tyr Glu Arg Asp Val Lys<br>310                      315                      320 | | 1078 |
| cct ctg cat agc gat ggc gca ttt ggt gga atg aca gac gaa gcc aaa<br>Pro Leu His Ser Asp Gly Ala Phe Gly Gly Met Thr Asp Glu Ala Lys<br>          325                      330                      335 | | 1126 |
| gct cgg gct cag aag atc cct aaa tct cgt tac gat ggc atc gat tct<br>Ala Arg Ala Gln Lys Ile Pro Lys Ser Arg Tyr Asp Gly Ile Asp Ser<br>340                      345                      350                      355 | | 1174 |
| ttc ctt ggt gat att cag aac gat ttc gca aaa gat ggg gaa gca gtg<br>Phe Leu Gly Asp Ile Gln Asn Asp Phe Ala Lys Asp Gly Glu Ala Val<br>                      360                      365                      370 | | 1222 |
| ttc aag tac ttc tct cca gag ttg aac gac atc agc cct cca atc aac<br>Phe Lys Tyr Phe Ser Pro Glu Leu Asn Asp Ile Ser Pro Pro Ile Asn<br>          375                      380                      385 | | 1270 |
| gag agg acg cta cag aga ctc gca cag gaa cct cag ttt gac cct gtc<br>Glu Arg Thr Leu Gln Arg Leu Ala Gln Glu Pro Gln Phe Asp Pro Val<br>                    390                      395                      400 | | 1318 |
| ctt gct cgt cac ttt gca cac ttg tac gtt cgt gat cca att gtg ata<br>Leu Ala Arg His Phe Ala His Leu Tyr Val Arg Asp Pro Ile Val Ile<br>405                      410                      415 | | 1366 |
| ttc gaa gaa cgt ata cac caa gac aat gac gat gaa acg gat cac ttt<br>Phe Glu Glu Arg Ile His Gln Asp Asn Asp Asp Glu Thr Asp His Phe<br>420                      425                      430                      435 | | 1414 |
| gag aac att caa tcc act aat tgg cag acg ttg agg ttc aag cca cca<br>Glu Asn Ile Gln Ser Thr Asn Trp Gln Thr Leu Arg Phe Lys Pro Pro<br>                      440                      445                      450 | | 1462 |
| act caa cag gca aca ccg gat aac aaa tcc gtt cca gga tgg aga gtg<br>Thr Gln Gln Ala Thr Pro Asp Asn Lys Ser Val Pro Gly Trp Arg Val<br>          455                      460                      465 | | 1510 |
| gaa ttc aga aca atg gag atc cag ctc aca gat ttt gag aat gct gct<br>Glu Phe Arg Thr Met Glu Ile Gln Leu Thr Asp Phe Glu Asn Ala Ala<br>                    470                      475                      480 | | 1558 |
| ttc tca atc ttc att gtt ctc ctg gga cag gca ata ctt gcg aca gat<br>Phe Ser Ile Phe Ile Val Leu Leu Gly Gln Ala Ile Leu Ala Thr Asp<br>485                      490                      495 | | 1606 |
| tcc aac tgg tac att cca atc tcc aag att gaa gat aac atg aaa cgt<br>Ser Asn Trp Tyr Ile Pro Ile Ser Lys Ile Glu Asp Asn Met Lys Arg<br>500                      505                      510                      515 | | 1654 |
| gca cat cac agg gac gca gta ttg aag gac aag ttc cat ttc aaa gct<br>Ala His His Arg Asp Ala Val Leu Lys Asp Lys Phe His Phe Lys Ala<br>                    520                      525                      530 | | 1702 |
| gat atc agc tcg cca gca ttc gac acg gtg gag ctg tca ctg gac gag<br>Asp Ile Ser Ser Pro Ala Phe Asp Thr Val Glu Leu Ser Leu Asp Glu<br>          535                      540                      545 | | 1750 |
| att gtc aat ggc tgc gat agc ttt atc gga ttg atg gca ctt gtg aag<br>Ile Val Asn Gly Cys Asp Ser Phe Ile Gly Leu Met Ala Leu Val Lys<br>                    550                      555                      560 | | 1798 |

```
aag cac ttg gaa tct cgc ttt gga att act ggt gac gac tta tcg cca      1846
Lys His Leu Glu Ser Arg Phe Gly Ile Thr Gly Asp Asp Leu Ser Pro
    565                 570                 575 aag ggt aca cac gct agg atc tac tac tac ttg gaa ttg atc tcc aag      1894
Lys Gly Thr His Ala Arg Ile Tyr Tyr Tyr Leu Glu Leu Ile Ser Lys
580                 585                 590                 595 aga gcc agt ggc gag cta cca act gct gct aaa ttc ata aga agg ttc      1942
Arg Ala Ser Gly Glu Leu Pro Thr Ala Ala Lys Phe Ile Arg Arg Phe
                600                 605                 610 ttg ctc gac cat aag gac tat caa cac gac tcc aaa ata act gct aga      1990
Leu Leu Asp His Lys Asp Tyr Gln His Asp Ser Lys Ile Thr Ala Arg
            615                 620                 625 atg aat tac gat ttg ttg aac acg ttg aat agc att tca gaa ctt ggc      2038
Met Asn Tyr Asp Leu Leu Asn Thr Leu Asn Ser Ile Ser Glu Leu Gly
        630                 635                 640 gaa gat gtt aga cag ttg ttg ggt gat gac att ggc aac tac ttg ata      2086
Glu Asp Val Arg Gln Leu Leu Gly Asp Asp Ile Gly Asn Tyr Leu Ile
    645                 650                 655 aac aac cca aag gct taatgacact aaggggagg aaactcgcca ttttgcatat        2141
Asn Asn Pro Lys Ala
660 aaacatagac aacgtcctat acagtattta attataaaag agttcagctc gtgatatcga    2201 tggatatgac gaccaagaca gct                                             2224

<210> SEQ ID NO 43
<211> LENGTH: 664
<212> TYPE: PRT
<213> ORGANISM: Candida utilis

<400> SEQUENCE: 43

Met Gly Leu Leu Ser Leu Gly Thr Pro Leu Pro Trp Glu Gln Thr Arg
1               5                   10                  15

Glu Tyr Ala Glu His Val Arg Thr Glu Gly Ile Glu Gln Leu Ile Lys
            20                  25                  30

Met Phe Lys Ala Ala Tyr Ala Arg Thr Gly Asp Gly Tyr Leu Trp Gly
        35                  40                  45

Asp Glu Val Glu Tyr Thr Leu Val Lys Phe Asp His Gly Arg Gly Leu
    50                  55                  60

Ala Leu Leu Ser Ile Asp Lys Asp Ser Val Leu Ala Asp Leu Asn Glu
65                  70                  75                  80

Gly Gly Ser Leu Ala Gln Leu Ser Val Asp Asn Asp Leu Asn Phe His
                85                  90                  95

Pro Glu Tyr Gly Arg Phe Met Leu Glu Ala Thr Pro Leu Ala Pro Tyr
            100                 105                 110

Asn Gly Asp Ser Leu Glu Asn Tyr Leu Tyr Val Glu Arg Asn Met Asn
        115                 120                 125

Ser Arg Arg Ser Val Ala Gln Thr Ala Ile Ala Asp Gly Thr Ile Lys
    130                 135                 140

Pro Leu Thr Ile Thr Val Tyr Pro Leu Met Gly Ile Asn Thr Phe Thr
145                 150                 155                 160

Phe Pro Ser Ala Val Ala Asn Gly Glu Ala Ser Gln Ser Leu Phe Leu
                165                 170                 175

Pro Asp Glu Ile Ile Asn Arg His Ala Arg Phe Pro Thr Leu Thr Ala
            180                 185                 190

Asn Ile Arg Lys Arg Arg Gly Glu Lys Val Ala Ile Asn Val Pro Leu
        195                 200                 205
```

```
Tyr Lys Asp Thr Asn Thr Leu Ser Ile Asp Glu Ser Ile Pro Lys Gly
    210                 215                 220

Arg Ser Leu Phe Lys His Asp Glu Glu Pro Glu Leu Gly Ala Ala Leu
225                 230                 235                 240

Pro Gly His Ile Tyr Met Asp Ser Met Gly Phe Gly Met Gly Cys Ser
                245                 250                 255

Cys Leu Gln Val Thr Val Gln Ala Pro Asn Leu Asn Arg Ala Arg Tyr
            260                 265                 270

Leu Tyr Asp Ser Trp Ala Asn Phe Ala Pro Leu Phe Leu Ala Leu Thr
        275                 280                 285

Ala Ala Ala Pro Val Phe Lys Gly His Leu Ala Asp Gln Asp Val Arg
290                 295                 300

Trp Asn Val Ile Ser Gly Ala Val Asp Asp Arg Thr Ala Tyr Glu Arg
305                 310                 315                 320

Asp Val Lys Pro Leu His Ser Asp Gly Ala Phe Gly Gly Met Thr Asp
                325                 330                 335

Glu Ala Lys Ala Arg Ala Gln Lys Ile Pro Lys Ser Arg Tyr Asp Gly
            340                 345                 350

Ile Asp Ser Phe Leu Gly Asp Ile Gln Asn Asp Phe Ala Lys Asp Gly
        355                 360                 365

Glu Ala Val Phe Lys Tyr Phe Ser Pro Glu Leu Asn Asp Ile Ser Pro
370                 375                 380

Pro Ile Asn Glu Arg Thr Leu Gln Arg Leu Ala Gln Glu Pro Gln Phe
385                 390                 395                 400

Asp Pro Val Leu Ala Arg His Phe Ala His Leu Tyr Val Arg Asp Pro
                405                 410                 415

Ile Val Ile Phe Glu Glu Arg Ile His Gln Asp Asn Asp Asp Glu Thr
            420                 425                 430

Asp His Phe Glu Asn Ile Gln Ser Thr Asn Trp Gln Thr Leu Arg Phe
        435                 440                 445

Lys Pro Pro Thr Gln Gln Ala Thr Pro Asp Asn Lys Ser Val Pro Gly
450                 455                 460

Trp Arg Val Glu Phe Arg Thr Met Glu Ile Gln Leu Thr Asp Phe Glu
465                 470                 475                 480

Asn Ala Ala Phe Ser Ile Phe Ile Val Leu Leu Gly Gln Ala Ile Leu
                485                 490                 495

Ala Thr Asp Ser Asn Trp Tyr Ile Pro Ile Ser Lys Ile Glu Asp Asn
            500                 505                 510

Met Lys Arg Ala His His Arg Asp Ala Val Leu Lys Asp Lys Phe His
        515                 520                 525

Phe Lys Ala Asp Ile Ser Ser Pro Ala Phe Asp Thr Val Glu Leu Ser
530                 535                 540

Leu Asp Glu Ile Val Asn Gly Cys Asp Ser Phe Ile Gly Leu Met Ala
545                 550                 555                 560

Leu Val Lys Lys His Leu Glu Ser Arg Phe Gly Ile Thr Gly Asp Asp
                565                 570                 575

Leu Ser Pro Lys Gly Thr His Ala Arg Ile Tyr Tyr Leu Glu Leu
            580                 585                 590

Ile Ser Lys Arg Ala Ser Gly Glu Leu Pro Thr Ala Lys Phe Ile
        595                 600                 605

Arg Arg Phe Leu Leu Asp His Lys Asp Tyr Gln His Asp Ser Lys Ile
610                 615                 620
```

```
Thr Ala Arg Met Asn Tyr Asp Leu Leu Asn Thr Leu Asn Ser Ile Ser
625                 630                 635                 640

Glu Leu Gly Glu Asp Val Arg Gln Leu Leu Gly Asp Asp Ile Gly Asn
            645                 650                 655

Tyr Leu Ile Asn Asn Pro Lys Ala
            660

<210> SEQ ID NO 44
<211> LENGTH: 2160
<212> TYPE: DNA
<213> ORGANISM: Saccharomyces cerevisiae
<220> FEATURE:
<221> NAME/KEY: CDS
<222> LOCATION: (1)..(2034)
<223> OTHER INFORMATION:

<400> SEQUENCE: 44
```

| | | | | | | | | | | | | | | | | |
|---|---|---|---|---|---|---|---|---|---|---|---|---|---|---|---|---|
| atg gga ctc tta gct ttg ggc acg cct ttg cag tgg ttt gag tct agg | | | | | | | | | | | | | | | | 48 |
| Met Gly Leu Leu Ala Leu Gly Thr Pro Leu Gln Trp Phe Glu Ser Arg | | | | | | | | | | | | | | | | |
| 1 | | | 5 | | | | | 10 | | | | | 15 | | | |

```
acg tac aat gaa cac ata agg gat gaa ggt atc gag cag ttg ttg tat      96
Thr Tyr Asn Glu His Ile Arg Asp Glu Gly Ile Glu Gln Leu Leu Tyr
                20                  25                  30 att ttc caa gct gct ggt aaa aga gac aat gac cct ctt ttt tgg gga     144
Ile Phe Gln Ala Ala Gly Lys Arg Asp Asn Asp Pro Leu Phe Trp Gly
            35                  40                  45 gac gag ctt gag tac atg gtt gta gat ttt gat gat aag gag aga aat     192
Asp Glu Leu Glu Tyr Met Val Val Asp Phe Asp Asp Lys Glu Arg Asn
        50                  55                  60 tct atg ctc gac gtt tgc cat gac aag ata ctc act gag ctt aat atg     240
Ser Met Leu Asp Val Cys His Asp Lys Ile Leu Thr Glu Leu Asn Met
65                  70                  75                  80 gag gat tcg tcc ctt tgt gag gct aac gat gtg agt ttt cac cct gag     288
Glu Asp Ser Ser Leu Cys Glu Ala Asn Asp Val Ser Phe His Pro Glu
                85                  90                  95 tat ggc cgg tat atg tta gag gca aca cca gct tct cca tat ttg aat     336
Tyr Gly Arg Tyr Met Leu Glu Ala Thr Pro Ala Ser Pro Tyr Leu Asn
            100                 105                 110 tac gtg ggt agt tac gtt gag gtt aac atg caa aaa aga cgt gcc att     384
Tyr Val Gly Ser Tyr Val Glu Val Asn Met Gln Lys Arg Arg Ala Ile
        115                 120                 125 gca gaa tat aag cta tct gaa tat gcg aga caa gat agt aaa aat aac     432
Ala Glu Tyr Lys Leu Ser Glu Tyr Ala Arg Gln Asp Ser Lys Asn Asn
    130                 135                 140 ttg cat gtg ggc tcc agg tct gtc cct ttg acg ctg act gtc ttc ccg     480
Leu His Val Gly Ser Arg Ser Val Pro Leu Thr Leu Thr Val Phe Pro
145                 150                 155                 160 agg atg gga tgc ccc gac ttt att aac att aag gat ccg tgg aat cat     528
Arg Met Gly Cys Pro Asp Phe Ile Asn Ile Lys Asp Pro Trp Asn His
                165                 170                 175 aaa aat gcc gct tcc agg tct ctg ttt tta ccc gat gaa gtc att aac     576
Lys Asn Ala Ala Ser Arg Ser Leu Phe Leu Pro Asp Glu Val Ile Asn
            180                 185                 190 aga cat gtc agg ttt cct aac ttg aca gca tcc atc agg acc agg cgt     624
Arg His Val Arg Phe Pro Asn Leu Thr Ala Ser Ile Arg Thr Arg Arg
        195                 200                 205 ggt gaa aaa gtt tgc atg aat gtt ccc atg tat aaa gat ata gct act     672
Gly Glu Lys Val Cys Met Asn Val Pro Met Tyr Lys Asp Ile Ala Thr
    210                 215                 220 cca gaa acg gat gac tcc atc tac gat cga gat tgg ttt tta cca gaa     720
Pro Glu Thr Asp Asp Ser Ile Tyr Asp Arg Asp Trp Phe Leu Pro Glu
```

```
                    225                 230                 235                 240 gac aaa gag gcg aaa ctg gct tcc aaa ccg ggt ttc att tat atg gat        768
Asp Lys Glu Ala Lys Leu Ala Ser Lys Pro Gly Phe Ile Tyr Met Asp
                245                 250                 255 tcc atg ggt ttt ggc atg ggc tgt tcg tgc tta caa gtg acc ttt cag        816
Ser Met Gly Phe Gly Met Gly Cys Ser Cys Leu Gln Val Thr Phe Gln
                    260                 265                 270 gca ccc aat atc aac aag gca cgt tac ctg tac gat gca tta gtg aat        864
Ala Pro Asn Ile Asn Lys Ala Arg Tyr Leu Tyr Asp Ala Leu Val Asn
                275                 280                 285 ttt gca cct ata atg cta gcc ttc tct gcc gct gcg cct gct ttt aaa        912
Phe Ala Pro Ile Met Leu Ala Phe Ser Ala Ala Ala Pro Ala Phe Lys
            290                 295                 300 ggt tgg cta gcc gac caa gat gtt cgt tgg aat gtg ata tct ggt gcg        960
Gly Trp Leu Ala Asp Gln Asp Val Arg Trp Asn Val Ile Ser Gly Ala
305                 310                 315                 320 gtg gac gac cgt act ccg aag gaa aga ggt gtt gcg cca tta cta ccc       1008
Val Asp Asp Arg Thr Pro Lys Glu Arg Gly Val Ala Pro Leu Leu Pro
                    325                 330                 335 aaa tac aac aag aac gga ttt gga ggc att gcc aaa gac gta caa gat       1056
Lys Tyr Asn Lys Asn Gly Phe Gly Gly Ile Ala Lys Asp Val Gln Asp
                340                 345                 350 aaa gtc ctt gaa ata cca aag tca aga tat agt tcg gtt gat ctt ttc       1104
Lys Val Leu Glu Ile Pro Lys Ser Arg Tyr Ser Ser Val Asp Leu Phe
            355                 360                 365 ttg ggt ggg tcg aaa ttt ttc aat agg act tat aac gac aca aat gta       1152
Leu Gly Gly Ser Lys Phe Phe Asn Arg Thr Tyr Asn Asp Thr Asn Val
        370                 375                 380 cct att aat gaa aaa gta tta gga cga cta cta gag aat gat aag gcg       1200
Pro Ile Asn Glu Lys Val Leu Gly Arg Leu Leu Glu Asn Asp Lys Ala
385                 390                 395                 400 cca ctg gac tat gat ctt gct aaa cat ttt gcg cat ctc tac ata aga       1248
Pro Leu Asp Tyr Asp Leu Ala Lys His Phe Ala His Leu Tyr Ile Arg
                    405                 410                 415 gat cca gta tct aca ttc gaa gaa ctg ttg aat cag gac aac aaa acg       1296
Asp Pro Val Ser Thr Phe Glu Glu Leu Leu Asn Gln Asp Asn Lys Thr
                420                 425                 430 tct tca aat cac ttt gaa aac atc caa agt aca aat tgg cag aca tta       1344
Ser Ser Asn His Phe Glu Asn Ile Gln Ser Thr Asn Trp Gln Thr Leu
            435                 440                 445 cgt ttt aaa ccc ccc aca caa caa gca acc ccg gac aaa aag gat tct       1392
Arg Phe Lys Pro Pro Thr Gln Gln Ala Thr Pro Asp Lys Lys Asp Ser
        450                 455                 460 cct ggt tgg aga gtg gaa ttc aga cca ttt gaa gtg caa cta tta gat       1440
Pro Gly Trp Arg Val Glu Phe Arg Pro Phe Glu Val Gln Leu Leu Asp
465                 470                 475                 480 ttt gag aac gct gcg tat tcc gtg ctc ata tac ttg att gtc gat agc       1488
Phe Glu Asn Ala Ala Tyr Ser Val Leu Ile Tyr Leu Ile Val Asp Ser
                    485                 490                 495 att ttg acc ttt tcc gat aat att aac gca tat att cat atg tcc aaa       1536
Ile Leu Thr Phe Ser Asp Asn Ile Asn Ala Tyr Ile His Met Ser Lys
                500                 505                 510 gta tgg gaa aat atg aag ata gcc cat cac aga gat gct atc cta ttt       1584
Val Trp Glu Asn Met Lys Ile Ala His His Arg Asp Ala Ile Leu Phe
            515                 520                 525 gaa aaa ttt cat tgg aaa aaa tca ttt cgc aac gac acc gat gtg gaa       1632
Glu Lys Phe His Trp Lys Lys Ser Phe Arg Asn Asp Thr Asp Val Glu
        530                 535                 540 act gaa gat tat tct ata agc gag att ttc cat aat cca gag aat ggt       1680
```

```
Thr Glu Asp Tyr Ser Ile Ser Glu Ile Phe His Asn Pro Glu Asn Gly
545                 550                 555                 560 ata ttt cct caa ttt gtt acg cca atc cta tgc caa aaa ggg ttt gta    1728
Ile Phe Pro Gln Phe Val Thr Pro Ile Leu Cys Gln Lys Gly Phe Val
                565                 570                 575 acc aaa gat tgg aaa gaa tta aag cat tct tcc aaa cac gag aga cta    1776
Thr Lys Asp Trp Lys Glu Leu Lys His Ser Ser Lys His Glu Arg Leu
            580                 585                 590 tac tat tat tta aag cta att tct gat aga gca agc ggt gaa ttg cca    1824
Tyr Tyr Tyr Leu Lys Leu Ile Ser Asp Arg Ala Ser Gly Glu Leu Pro
        595                 600                 605 aca aca gca aaa ttc ttt aga aat ttt gta cta caa cat cca gat tac    1872
Thr Thr Ala Lys Phe Phe Arg Asn Phe Val Leu Gln His Pro Asp Tyr
    610                 615                 620 aaa cat gat tca aaa att tca aag tcg atc aat tat gat ttg ctt tct    1920
Lys His Asp Ser Lys Ile Ser Lys Ser Ile Asn Tyr Asp Leu Leu Ser
625                 630                 635                 640 acg tgt gat aga ctt acc cat tta gac gat tca aaa ggt gaa ttg aca    1968
Thr Cys Asp Arg Leu Thr His Leu Asp Asp Ser Lys Gly Glu Leu Thr
                645                 650                 655 tcc ttt tta gga gct gaa att gca gaa tat gta aaa aaa aat aag cct    2016
Ser Phe Leu Gly Ala Glu Ile Ala Glu Tyr Val Lys Lys Asn Lys Pro
            660                 665                 670 tca ata gaa agc aaa tgt taaactcctt ttacttcggt tgtgaaagaa           2064
Ser Ile Glu Ser Lys Cys
        675 agttgacatt atcgatttgg gtgacacggt gattgaaaaa gcaacgacca gtattatacc  2124 tctttttttt attattcagt ttatattttt gcaagt                            2160

<210> SEQ ID NO 45
<211> LENGTH: 678
<212> TYPE: PRT
<213> ORGANISM: Saccharomyces cerevisiae

<400> SEQUENCE: 45

Met Gly Leu Leu Ala Leu Gly Thr Pro Leu Gln Trp Phe Glu Ser Arg
1               5                   10                  15

Thr Tyr Asn Glu His Ile Arg Asp Glu Gly Ile Glu Gln Leu Leu Tyr
            20                  25                  30

Ile Phe Gln Ala Ala Gly Lys Arg Asp Asn Asp Pro Leu Phe Trp Gly
        35                  40                  45

Asp Glu Leu Glu Tyr Met Val Val Asp Phe Asp Lys Glu Arg Asn
    50                  55                  60

Ser Met Leu Asp Val Cys His Asp Lys Ile Leu Thr Glu Leu Asn Met
65                  70                  75                  80

Glu Asp Ser Ser Leu Cys Glu Ala Asn Asp Val Ser Phe His Pro Glu
                85                  90                  95

Tyr Gly Arg Tyr Met Leu Glu Ala Thr Pro Ala Ser Pro Tyr Leu Asn
            100                 105                 110

Tyr Val Gly Ser Tyr Val Glu Val Asn Met Gln Lys Arg Arg Ala Ile
        115                 120                 125

Ala Glu Tyr Lys Leu Ser Glu Tyr Ala Arg Gln Asp Ser Lys Asn Asn
    130                 135                 140

Leu His Val Gly Ser Arg Ser Val Pro Leu Thr Leu Thr Val Phe Pro
145                 150                 155                 160

Arg Met Gly Cys Pro Asp Phe Ile Asn Ile Lys Asp Pro Trp Asn His
                165                 170                 175
```

```
Lys Asn Ala Ala Ser Arg Ser Leu Phe Leu Pro Asp Glu Val Ile Asn
            180                 185                 190
Arg His Val Arg Phe Pro Asn Leu Thr Ala Ser Ile Arg Thr Arg Arg
        195                 200                 205
Gly Glu Lys Val Cys Met Asn Val Pro Met Tyr Lys Asp Ile Ala Thr
    210                 215                 220
Pro Glu Thr Asp Asp Ser Ile Tyr Asp Arg Asp Trp Phe Leu Pro Glu
225                 230                 235                 240
Asp Lys Glu Ala Lys Leu Ala Ser Lys Pro Gly Phe Ile Tyr Met Asp
                245                 250                 255
Ser Met Gly Phe Gly Met Gly Cys Ser Cys Leu Gln Val Thr Phe Gln
            260                 265                 270
Ala Pro Asn Ile Asn Lys Ala Arg Tyr Leu Tyr Asp Ala Leu Val Asn
        275                 280                 285
Phe Ala Pro Ile Met Leu Ala Phe Ser Ala Ala Pro Ala Phe Lys
    290                 295                 300
Gly Trp Leu Ala Asp Gln Asp Val Arg Trp Asn Val Ile Ser Gly Ala
305                 310                 315                 320
Val Asp Asp Arg Thr Pro Lys Glu Arg Gly Val Ala Pro Leu Leu Pro
                325                 330                 335
Lys Tyr Asn Lys Asn Gly Phe Gly Gly Ile Ala Lys Asp Val Gln Asp
            340                 345                 350
Lys Val Leu Glu Ile Pro Lys Ser Arg Tyr Ser Ser Val Asp Leu Phe
        355                 360                 365
Leu Gly Gly Ser Lys Phe Phe Asn Arg Thr Tyr Asn Asp Thr Asn Val
    370                 375                 380
Pro Ile Asn Glu Lys Val Leu Gly Arg Leu Leu Glu Asn Asp Lys Ala
385                 390                 395                 400
Pro Leu Asp Tyr Asp Leu Ala Lys His Phe Ala His Leu Tyr Ile Arg
                405                 410                 415
Asp Pro Val Ser Thr Phe Glu Glu Leu Leu Asn Gln Asp Asn Lys Thr
            420                 425                 430
Ser Ser Asn His Phe Glu Asn Ile Gln Ser Thr Asn Trp Gln Thr Leu
        435                 440                 445
Arg Phe Lys Pro Pro Thr Gln Gln Ala Thr Pro Asp Lys Lys Asp Ser
    450                 455                 460
Pro Gly Trp Arg Val Glu Phe Arg Pro Phe Glu Val Gln Leu Leu Asp
465                 470                 475                 480
Phe Glu Asn Ala Ala Tyr Ser Val Leu Ile Tyr Leu Ile Val Asp Ser
                485                 490                 495
Ile Leu Thr Phe Ser Asp Asn Ile Asn Ala Tyr Ile His Met Ser Lys
            500                 505                 510
Val Trp Glu Asn Met Lys Ile Ala His His Arg Asp Ala Ile Leu Phe
        515                 520                 525
Glu Lys Phe His Trp Lys Lys Ser Phe Arg Asn Asp Thr Asp Val Glu
    530                 535                 540
Thr Glu Asp Tyr Ser Ile Ser Glu Ile Phe His Asn Pro Glu Asn Gly
545                 550                 555                 560
Ile Phe Pro Gln Phe Val Thr Pro Ile Leu Cys Gln Lys Gly Phe Val
                565                 570                 575
Thr Lys Asp Trp Lys Glu Leu Lys His Ser Ser Lys His Glu Arg Leu
            580                 585                 590
```

```
Tyr Tyr Tyr Leu Lys Leu Ile Ser Asp Arg Ala Ser Gly Glu Leu Pro
        595                 600                 605

Thr Thr Ala Lys Phe Phe Arg Asn Phe Val Leu Gln His Pro Asp Tyr
    610                 615                 620

Lys His Asp Ser Lys Ile Ser Lys Ser Ile Asn Tyr Asp Leu Leu Ser
625                 630                 635                 640

Thr Cys Asp Arg Leu Thr His Leu Asp Asp Ser Lys Gly Glu Leu Thr
                645                 650                 655

Ser Phe Leu Gly Ala Glu Ile Ala Glu Tyr Val Lys Lys Asn Lys Pro
            660                 665                 670

Ser Ile Glu Ser Lys Cys
        675

<210> SEQ ID NO 46
<211> LENGTH: 21
<212> TYPE: DNA
<213> ORGANISM: Artificial Sequence
<220> FEATURE:
<223> OTHER INFORMATION: Synthetic DNA

<400> SEQUENCE: 46
gtggacgacc gtactccgaa g                                             21

<210> SEQ ID NO 47
<211> LENGTH: 21
<212> TYPE: DNA
<213> ORGANISM: Artificial Sequence
<220> FEATURE:
<223> OTHER INFORMATION: Synthetic DNA

<400> SEQUENCE: 47
acccaaatcg ataatgtcaa c                                             21

<210> SEQ ID NO 48
<211> LENGTH: 36
<212> TYPE: DNA
<213> ORGANISM: Artificial Sequence
<220> FEATURE:
<223> OTHER INFORMATION: Synthetic DNA

<400> SEQUENCE: 48
cttttcttgg gtgggtagta attttttcaat aggact                            36

<210> SEQ ID NO 49
<211> LENGTH: 36
<212> TYPE: DNA
<213> ORGANISM: Artificial Sequence
<220> FEATURE:
<223> OTHER INFORMATION: Synthetic DNA

<400> SEQUENCE: 49
agtcctattg aaaaattact acccacccaa gaaaag                             36

<210> SEQ ID NO 50
<211> LENGTH: 35
<212> TYPE: DNA
<213> ORGANISM: Artificial Sequence
<220> FEATURE:
<223> OTHER INFORMATION: Synthetic DNA

<400> SEQUENCE: 50
gagtacggta ccatggggct gctatcatta gggac                              35
```

```
<210> SEQ ID NO 51
<211> LENGTH: 34
<212> TYPE: DNA
<213> ORGANISM: Artificial Sequence
<220> FEATURE:
<223> OTHER INFORMATION: Synthetic DNA

<400> SEQUENCE: 51
cccttatcta gattaagcct ttgggttgtt tatc                               34
```